(12) United States Patent
Witztum et al.

(10) Patent No.: US 11,530,259 B2
(45) Date of Patent: Dec. 20, 2022

(54) THERAPIES AND METHODS TO TREAT TLR2-MEDIATED DISEASES AND DISORDERS

(71) Applicant: The Regents of the University of California, Oakland, CA (US)

(72) Inventors: Joseph L. Witztum, San Diego, CA (US); Sotirios Tsimikas, San Diego, CA (US); Xuchu Que, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/965,271

(22) PCT Filed: Jan. 29, 2019

(86) PCT No.: PCT/US2019/015723
§ 371 (c)(1),
(2) Date: Jul. 27, 2020

(87) PCT Pub. No.: WO2019/148204
PCT Pub. Date: Aug. 1, 2019

(65) Prior Publication Data
US 2021/0155679 A1 May 27, 2021

Related U.S. Application Data

(60) Provisional application No. 62/623,276, filed on Jan. 29, 2018.

(51) Int. Cl.
| | |
|---|---|
| *C07K 16/18* | (2006.01) |
| *A61P 37/06* | (2006.01) |
| *A61K 9/00* | (2006.01) |
| *A61K 31/60* | (2006.01) |
| *A61K 39/395* | (2006.01) |

(52) U.S. Cl.
CPC ............ *C07K 16/18* (2013.01); *A61K 9/0019* (2013.01); *A61K 31/60* (2013.01); *A61K 39/39516* (2013.01); *A61K 39/39533* (2013.01); *A61P 37/06* (2018.01); *C07K 2317/51* (2013.01); *C07K 2317/515* (2013.01); *C07K 2317/52* (2013.01); *C07K 2317/524* (2013.01); *C07K 2317/565* (2013.01); *C07K 2317/622* (2013.01); *C07K 2317/76* (2013.01)

(58) Field of Classification Search
None
See application file for complete search history.

(56) References Cited

U.S. PATENT DOCUMENTS

| | | | | |
|---|---|---|---|---|
| 2012/0230911 A1* | 9/2012 | Hsieh | ..................... | A61P 31/02 |
| | | | | 424/1.49 |
| 2015/0196663 A1* | 7/2015 | Shusta | ................. | A61K 9/0085 |
| | | | | 424/178.1 |
| 2015/0266947 A1* | 9/2015 | Sierks | ................ | G01N 33/6896 |
| | | | | 424/135.1 |
| 2015/0376268 A1 | 12/2015 | Witztum et al. | | |
| 2017/0355756 A1* | 12/2017 | Julien | ..................... | A61P 25/28 |

FOREIGN PATENT DOCUMENTS

| | | | |
|---|---|---|---|
| RU | 2577228 C2 | | 3/2016 |
| WO | WO 2008068048 | * | 6/2008 |
| WO | 2011/031460 A2 | | 3/2011 |
| WO | 2011/160845 A2 | | 12/2011 |
| WO | 2014/131034 A2 | | 8/2014 |

OTHER PUBLICATIONS

Wikipedia "single-chain variable fragment" accessed from wikipedia. org on Dec. 15, 2021 (Year: 2021).*
Chen "Enhancement and destruction of antibody function by somatic mutation: unequal occurrence is controlled by V gene combinatorial associations" EMBO 14(12):2784-2794 (Year: 1995).*
Kussie "A Single Engineered Amino Acid Substitution Changes Antibody Fine Specificity" J immunol 152(1):146-52 (Year: 1994).*
Rossi "Tumor necrosis factor is elevated in progressive multiple sclerosis and causes excitotoxic neurodegeneration" Multiple Sclerosis Journal 2014, vol. 20(3) 304—(Year: 2014).*
Abe "Gene Expression Profiling of the Effect of High-Dose Intravenous Ig in Patients with Kawasaki disease" J Immunol 2005; 174:5837-5845 (Year: 2005).*
Cedar "Researchers Link KawasakiDisease in Childhood withIncreased Risk of AdultHeart Disease" accessed from cedars-sinai.org on Dec. 15, 2021 (Year: 2012).*
Leitinger "Oxidized phospholipids as triggers of inflammation in atherosclerosis" mol nutrfood res 49:1063-1071 (Year: 2005).*
Wittmann-Regis, Agnes, International Preliminary Report on Patentability and Written Opinion, PCT/US2019/015723, The International Bureau of WIPO, dated Aug. 13, 2020.
Kadl et al., "Oxidized phospholipid-induced Inflammation is mediated by Toll-like receptor 2," Free Radic. Biol. Med., 51(10); 1903-1909, 2011.
Mortazavi et al., "Down-regulation of TLR2, 3, 9 and Signaling Mediators, MyD88 and TRIF, Gene Transcript Levels in Patients with Kawasaki Disease Treated with IVIG," Iran J. Allergy Asthma Immunol. 14(2): 188-197, 2015.
Seimon et al., "Atherogenic Lipids and Lipoproteins Trigger CD36-TLR2-Dependent Apoptosis in Macrophages Undergoing Endoplasmic Reticulum Stress," Cell Metabolism, 12(5): 467-482, 2010.
Young, Lee W., International Search Report and Written Opinion, PCT/US2019/015723, U.S. Patent & Trademark Office, dated Jun. 24, 2019.

(Continued)

*Primary Examiner* — Adam Weidner
(74) *Attorney, Agent, or Firm* — Gavrilovich, Dodd & Lindsey LLP

(57) ABSTRACT

The disclosure provides for methods and treatments of TLR2-mediated diseases and disorders comprising administering an antibody, antibody fragment, or polypeptide that binds to and inhibits the biological activity of oxidized phospholipids.

14 Claims, 23 Drawing Sheets
Specification includes a Sequence Listing.

(56) References Cited

OTHER PUBLICATIONS

Fellows, Edward, Extended European Search Report, European Patent Office, Application No. 19744139.7, dated Dec. 22, 2021.
Scherler et al., "Acute phase of Kawasaki disease: a review of national guideline recommendations," Euro. J. of Pediatrics, 181: 2563-2673, 2022.
Mariuzza et al., "The Structural Basis of Antigen-Antibody Recognition", Am. Rev. Biophys. Chem., Jun. 1987, 16:139-59.
Roitt et al., Immunology, Fifth Edition, Mar. 2000, 7 pages.
Nazina, E.C. Office Action and Search Report, Russian Patent Office, Application No. 2020125162, dated Aug. 11, 2022.

* cited by examiner

>E06scFv antibody fragment
(From 1 to 930. Translation 309 a.a. MW=33.65 kDa)

```
  1 ATGGAGACAGACACACTCCTGCTATGGGTACTGCTGCTCTGGGTTCCAGGTTCCACTGGTGACGCGGCCCAGCCG
  1  M  E  T  D  T  L  L  L  W  V  L  L  L  W  V  P  G  S  T  G  D  A  A  Q  P
 76 GCCAGGCGCGCCGTACGAAGCTTAGACATTGTGATGACTCAGTCTCCATCTTCCCTTTCTGTGTCAGCAGGTAAG
 26  A  R  R  A  V  R  S  L  D  I  V  M  T  Q  S  P  S  S  L  S  V  S  A  G  K
151 AAGGTCACCATTAGTTGCACGGCCAGTGAGAGCCTTTATTCAAGCAAACACAAGGTGCACTACTTGGCTTGGTAC
 51  K  V  T  I  S  C  T  A  S  E  S  L  Y  S  S  K  H  K  V  H  Y  L  A  W  Y
226 CAGAAGAAACCAGAGCAATCTCCTAAACTGCTGATATACGGGGCATCCAACCGATACATTGGGGTCCCTGATCGC
 76  Q  K  K  P  E  Q  S  P  K  L  L  I  Y  G  A  S  N  R  Y  I  G  V  P  D  R
301 TTCACAGGCAGTGGATCTGGGACAGATTTCACTCTGACCATCAGCAGTGTACAGGTTGAAGACCTCACACATTAT
101  F  T  G  S  G  S  G  T  D  F  T  L  T  I  S  S  V  Q  V  E  D  L  T  H  Y
376 TACTGTGCACAGTTTTACAGCTATCCGCTCACGTTCGGTGCTGGGACCAAGCTGGAAATCAAAGGTGGTGGAGGA
126  Y  C  A  Q  F  Y  S  Y  P  L  T  F  G  A  G  T  K  L  E  I  K  G  G  G  G
451 TCAGGTGGAGGTGGTTCAGGAGGTGGCGGATCCGAGGTGAAGCTGGTGGAGTCTGGAGGAGGCTTGGTACAGCCT
151  S  G  G  G  G  S  G  G  G  G  S  E  V  K  L  V  E  S  G  G  G  L  V  Q  P
526 GGGGGTTCTCTGAGACTCTCCTGTGCAACTTCTGGGTTCACCTTCAGTGATTTCTACATGGAGTGGGTCCGCCAG
176  G  G  S  L  R  L  S  C  A  T  S  G  F  T  F  S  D  F  Y  M  E  W  V  R  Q
601 GCTCCAGGGAAGAGACTGGAGTGGATTGCTGCAAGTAGAAACAAAGCTAATGATTATACAACAGAGTACGCTGAC
201  A  P  G  K  R  L  E  W  I  A  A  S  R  N  K  A  N  D  Y  T  T  E  Y  A  D
676 TCTGTGAAGGGTCGGTTCATCGTCTCCAGAGACACTTCCCAAAGCATCCTCTACCTTCAGATGAATGCCCTGAGA
226  S  V  K  G  R  F  I  V  S  R  D  T  S  Q  S  I  L  Y  L  Q  M  N  A  L  R
751 GCCGAGGACACTGCCATTTATTACTGTGCAAGAGATTACTACGGTAGTAGCTACTGGTACTTCGATGTCTGGGGC
251  A  E  D  T  A  I  Y  Y  C  A  R  D  Y  Y  G  S  S  Y  W  Y  F  D  V  W  G
826 GCAGGGACCACGGTCACCGTCTCCTCTCGAGGAGGGCCCGAACAAAAACTCATCTCAGAAGAGGATCTGAATAGC
276  A  G  T  T  V  T  V  S  S  R  G  G  P  E  Q  K  L  I  S  E  E  D  L  N  S
901 GCCGTCGACCATCATCATCATCATCATTGA
301  A  V  D  H  H  H  H  H  H  *
```

Annotation:
A.A. 1 … 33 = Ig kappa chain leader sequence for antibody secretion.
A.A. 34 … 146 = E06 light-chain variable region.
A.A. 42 … 49 = FW1 region TFLAVTAS mutated to SSLSVSAG to enhance affinity to OxPL-PC/OxLDL and functional activity.
A.A. 57 … 73 = "TASESLYSSKHKVHYLA" E06 L-chain CDR1.
A.A. 89 … 95 = "GASNRYI" E06 L-chain CDR2.
A.A. 127 … 136 = "CAQFYSYPLT" E06 L-chain CDR3.
A.A. 147 … 161 = (Gly4Ser)x3 flexible linker peptides.
A.A. 162 … 284 = E06 heavy-chain variable region with triple mutations of P201A, S224A and A225D to       increase antibody affinity to OxPL-PC/OxLDL.
A.A. 187 … 193 = "GFTFSDF" E06 H-chain CDR1.
A.A. 213 … 220 = "RNKANDYT" E06 H-chain CDR2.
A.A. 259 … 274 = "CARDYYGSSYWYFDVW" E06 H-chain CDR3.
A.A. 289 … 298 = myc epitope tag
A.A. 304 … 309 = polyHis tag.

*FIG. 2*

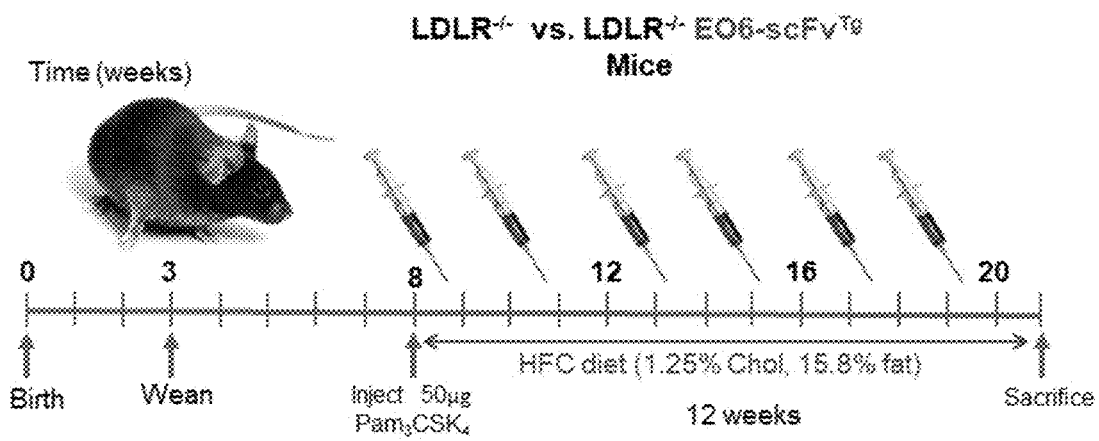
FIG. 3
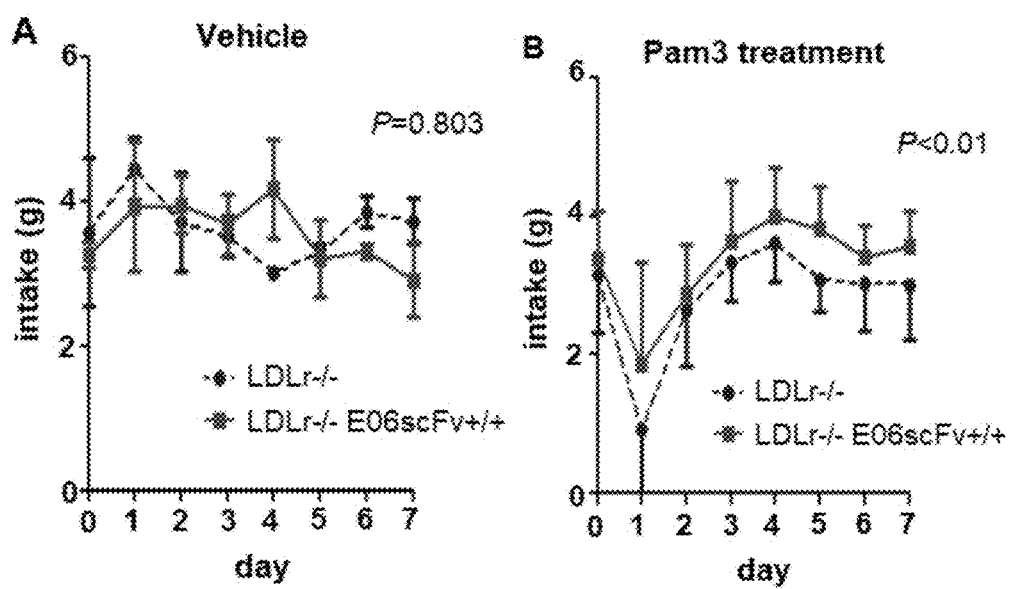
FIG. 4A-B

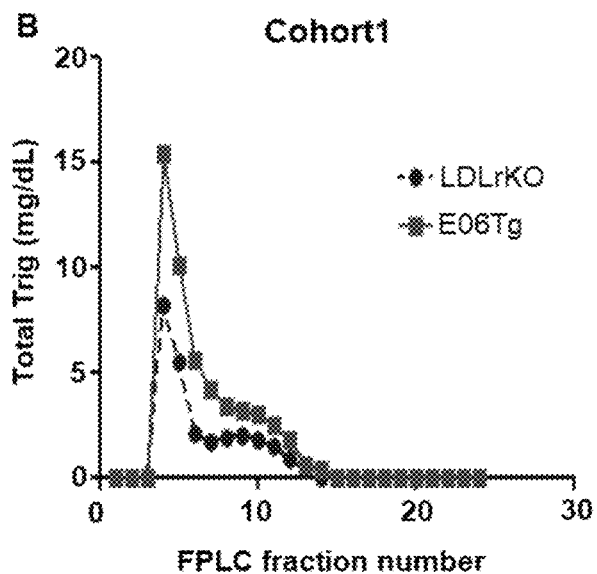
FIG. 6B
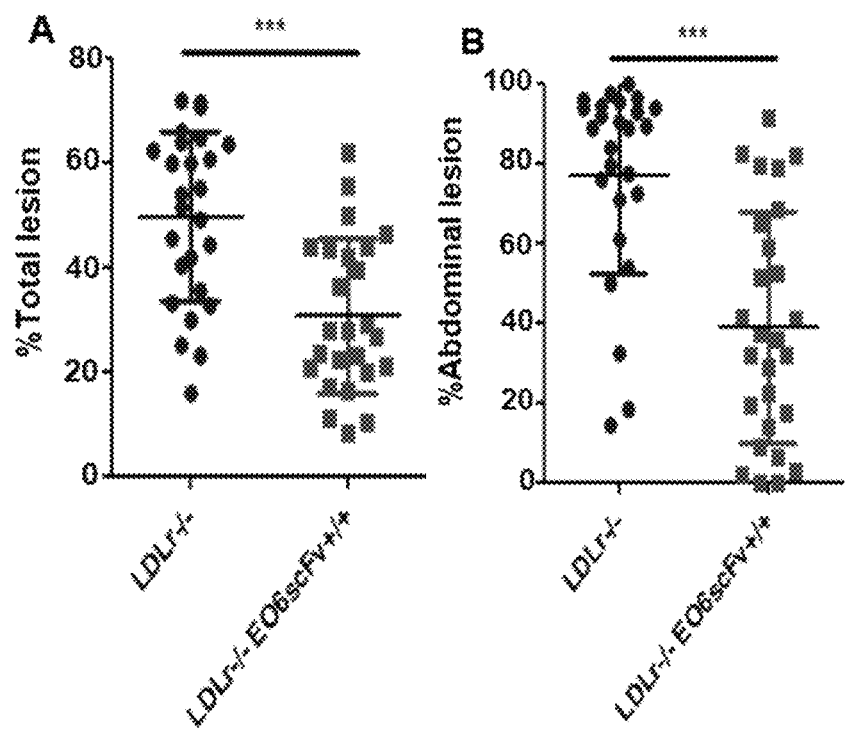
FIG. 7A-B

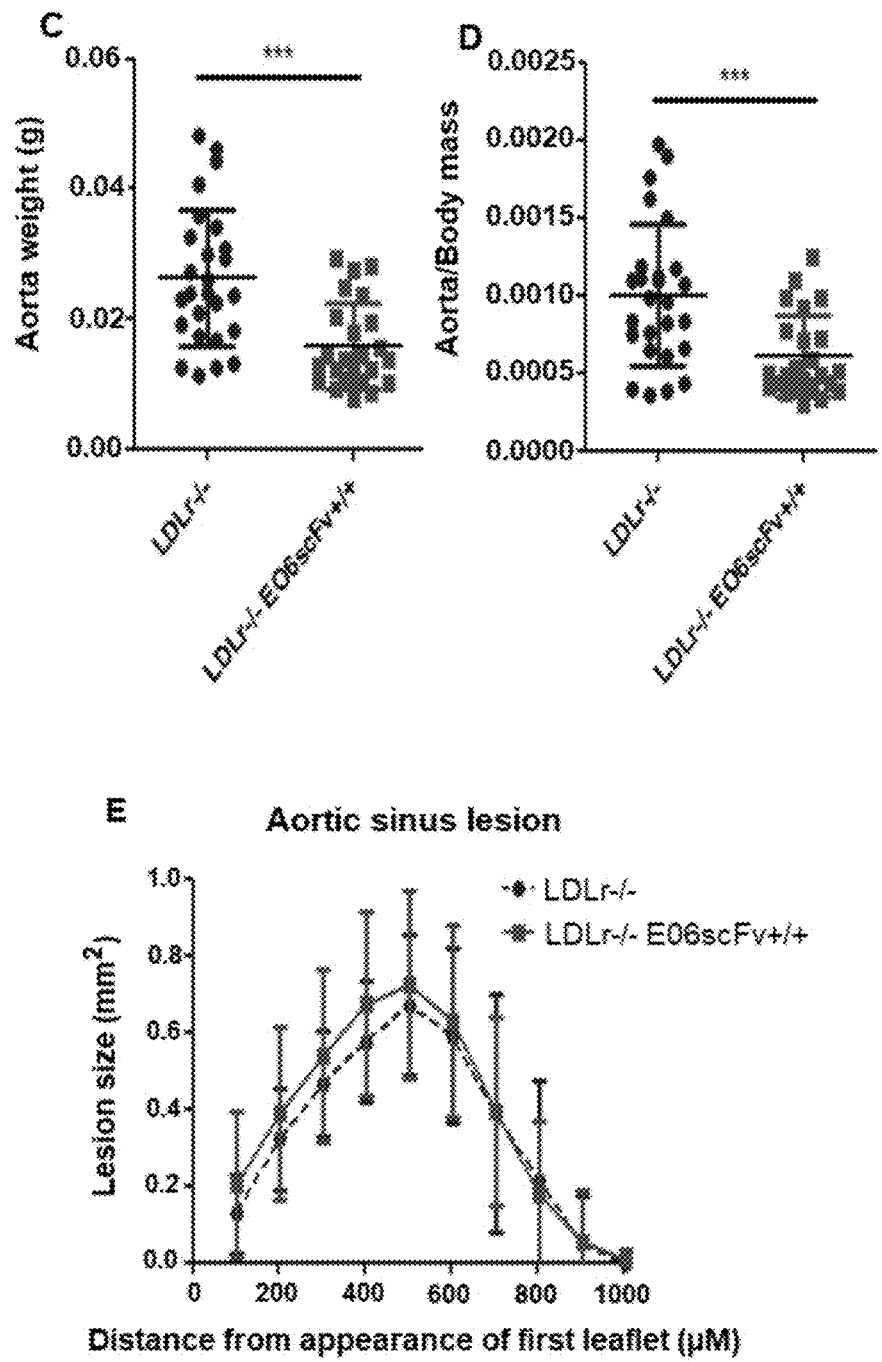
FIG. 7C-E

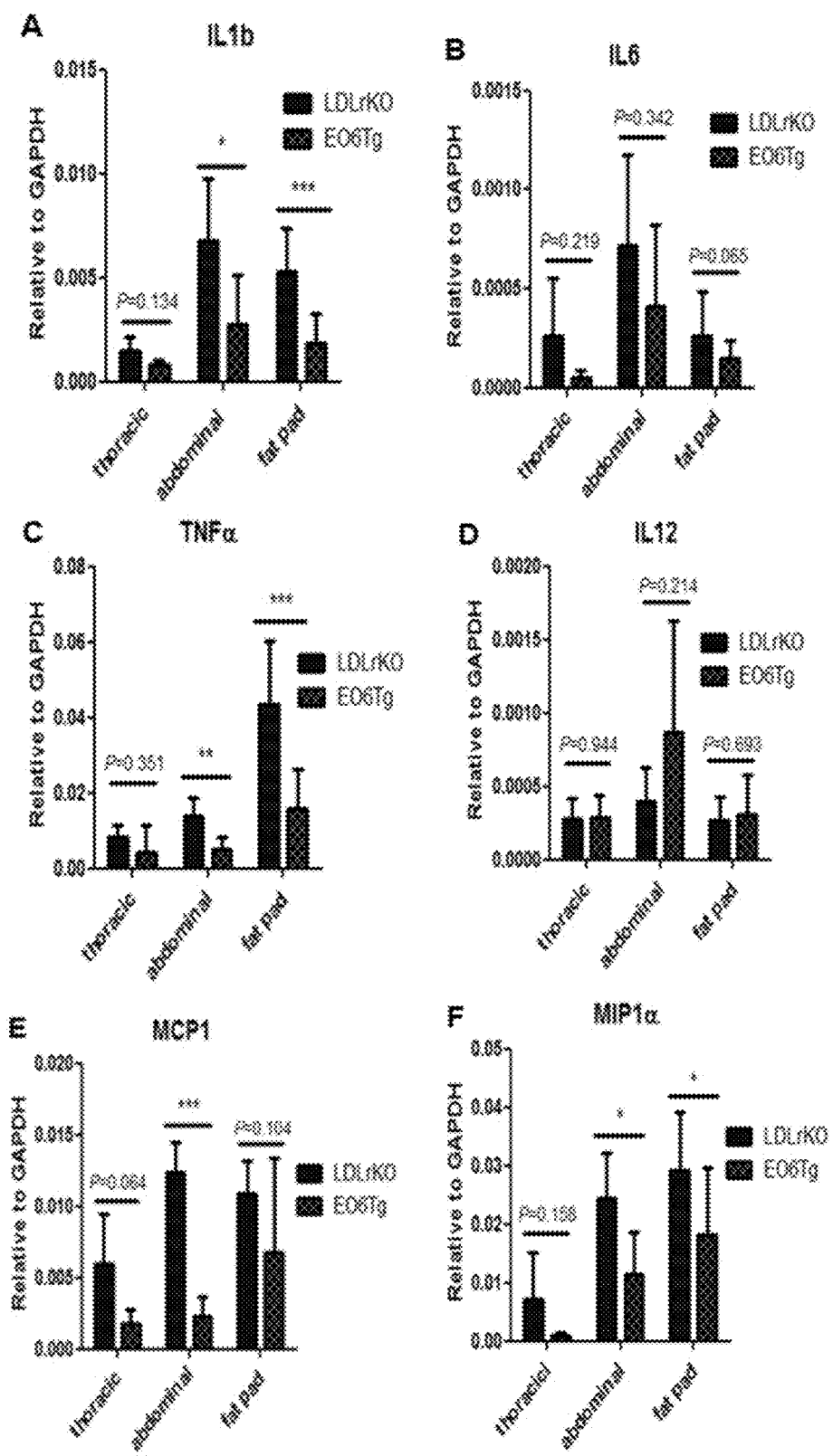
FIG. 8A-F

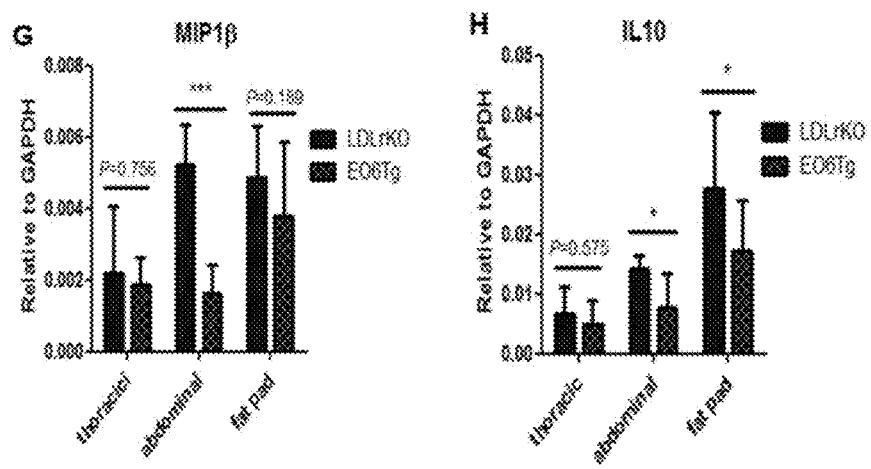
FIG. 8G-H
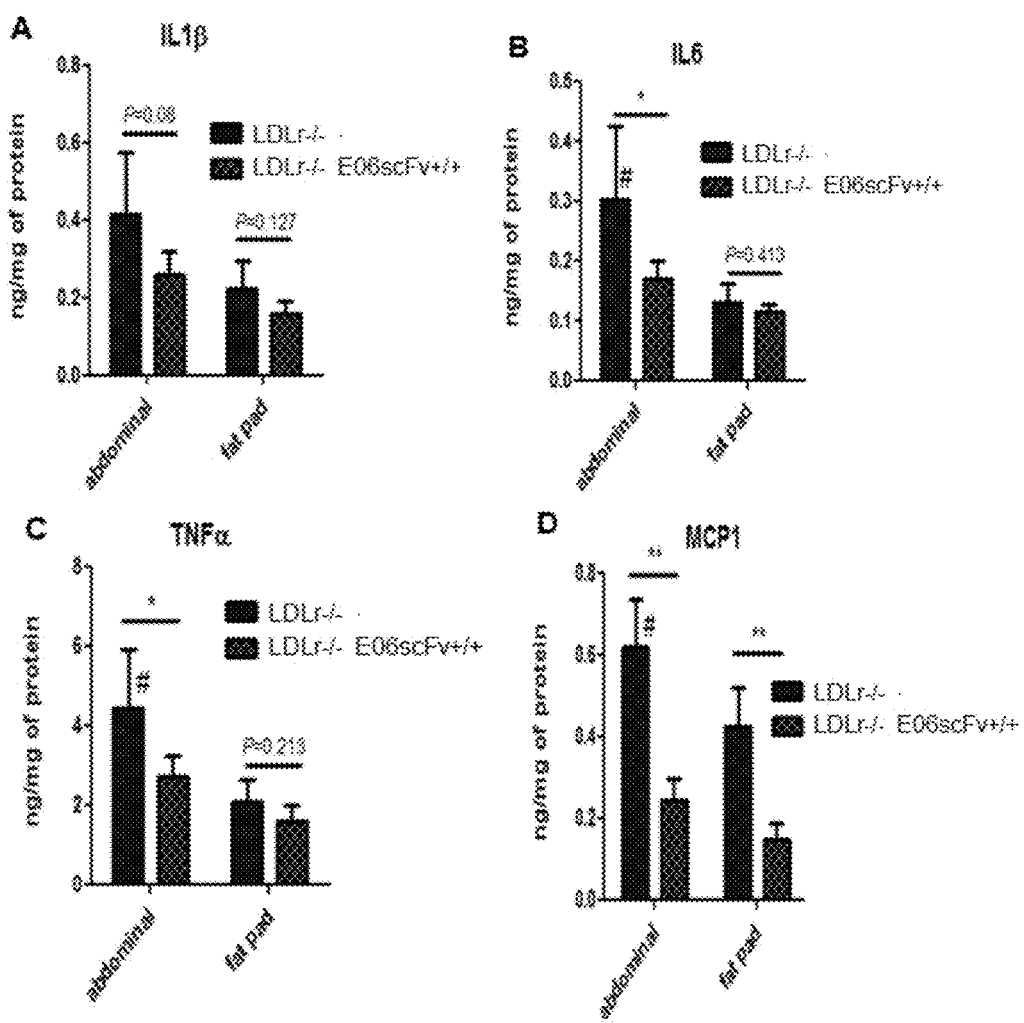
FIG. 9A-D

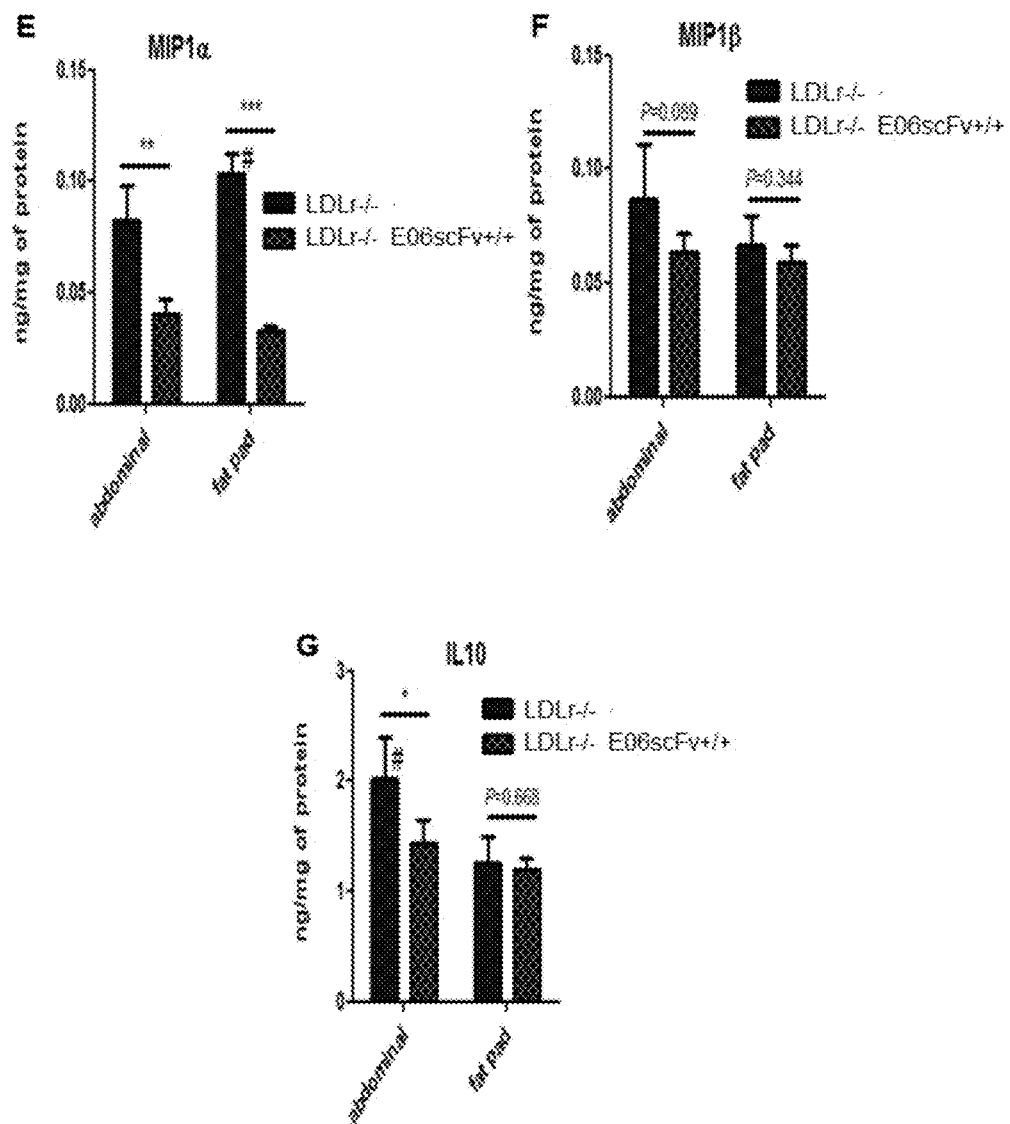
FIG. 9E-G

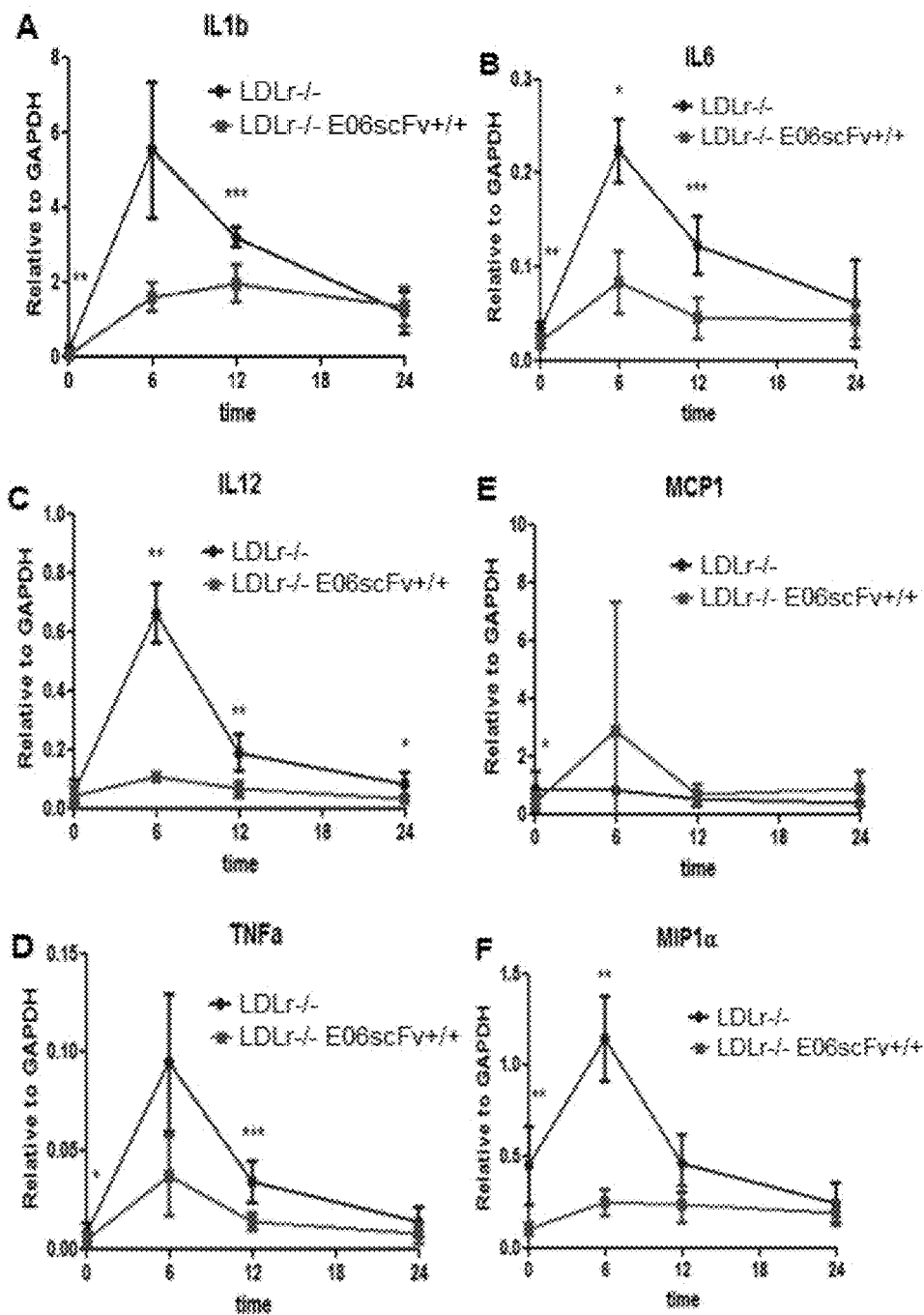
FIG. 10A-F

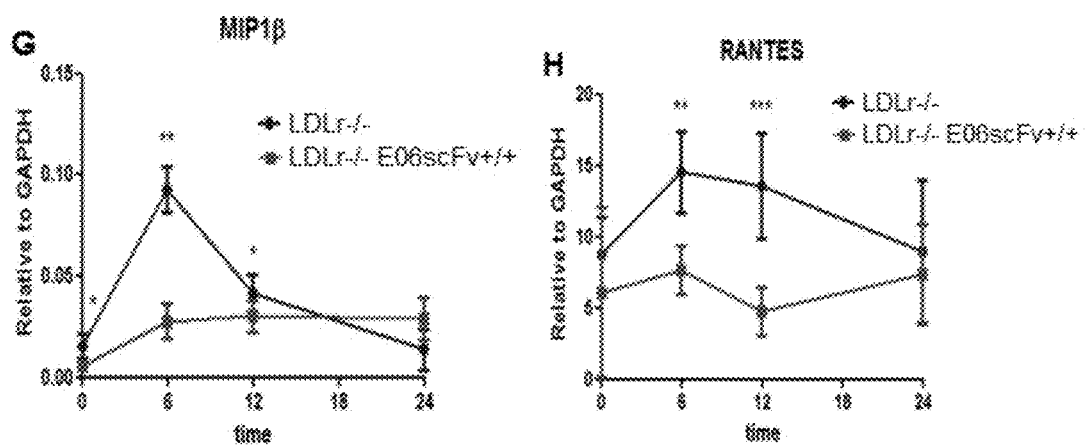
FIG. 10G-H
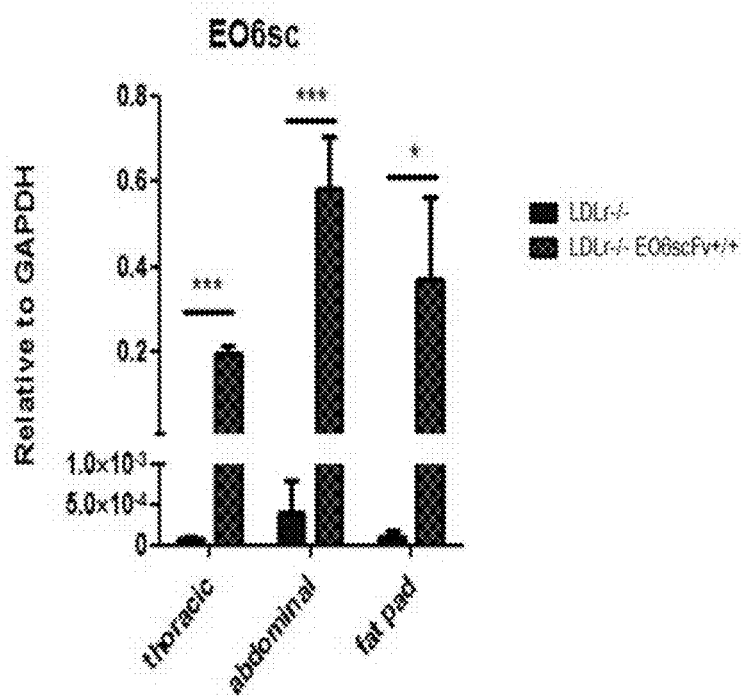
FIG. 11

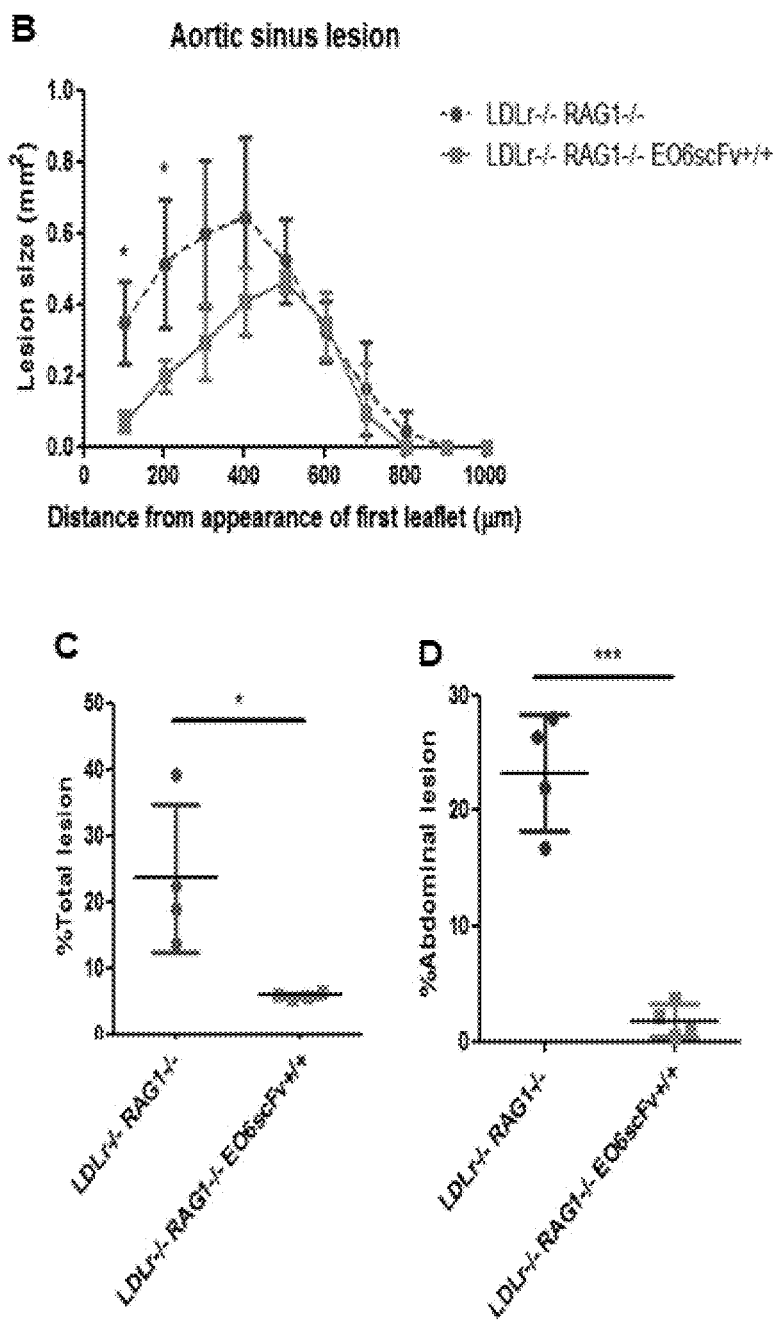
FIG. 13B-D

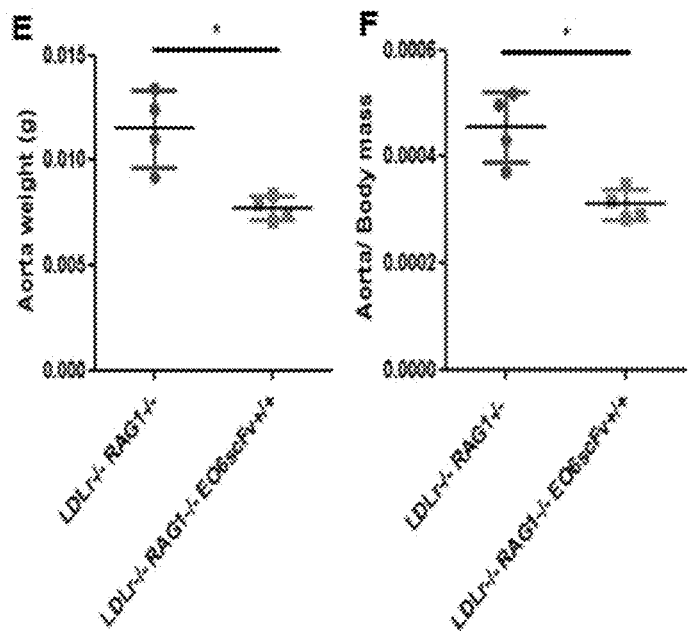
FIG. 13E-F
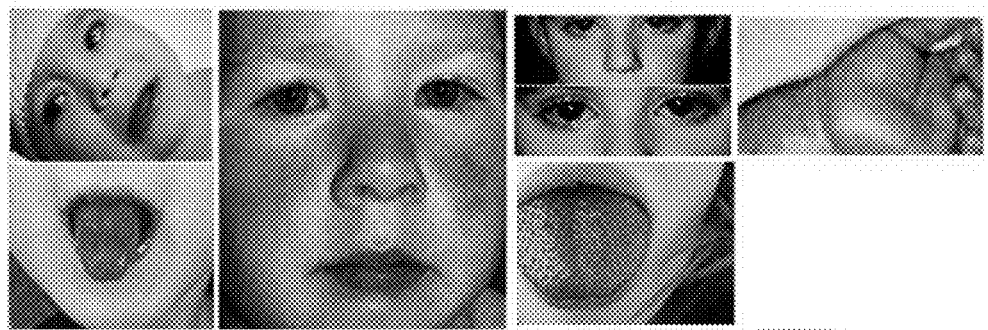
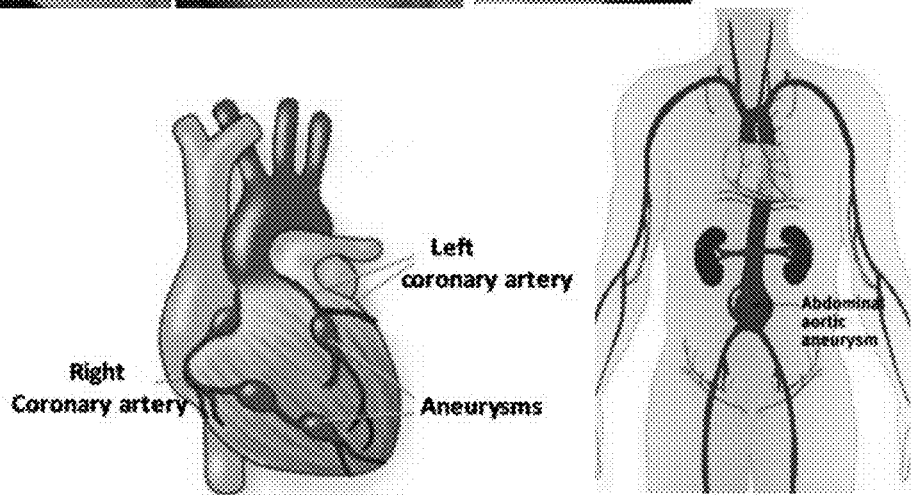
FIG. 14

TLR2-/- LDLR-/-
KD11-4
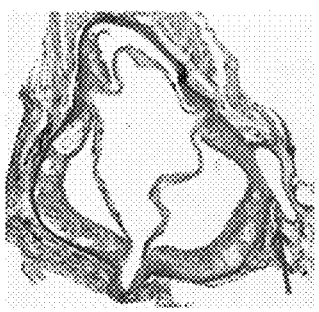
KD10-4
KD12-5
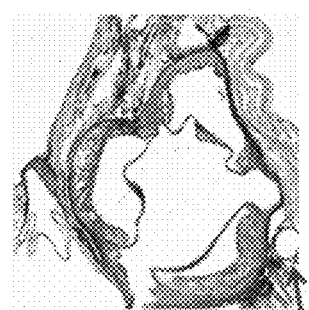
KD13-4
IK17-Tg LDLR-/-
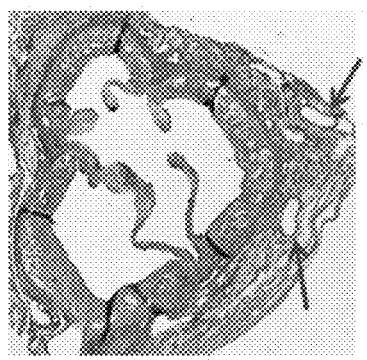
KD31-5
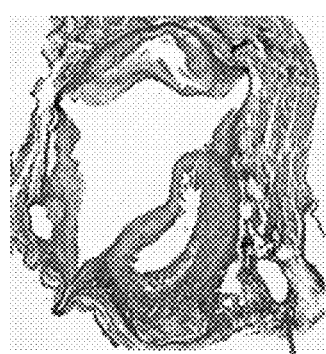
KD29-2
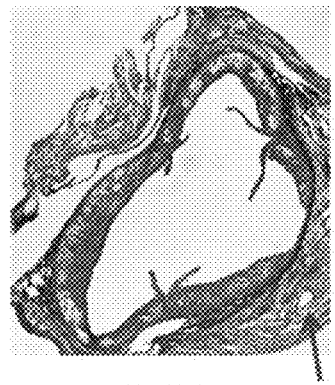
KD30-6
FIG. 21

SEQUENCE LISTING

```
<160> NUMBER OF SEQ ID NOS: 14

<210> SEQ ID NO 1
<211> LENGTH: 930
<212> TYPE: DNA
<213> ORGANISM: Artificial Sequence
<220> FEATURE:
<223> OTHER INFORMATION: Engineered scFV E06 Antibody domain
<220> FEATURE:
<221> NAME/KEY: CDS
<222> LOCATION: (1)..(930)

<400> SEQUENCE: 1 atg gag aca gac aca ctc ctg cta tgg gta ctg ctg ctc tgg gtt cca         48
Met Glu Thr Asp Thr Leu Leu Leu Trp Val Leu Leu Leu Trp Val Pro
1               5                   10                  15 ggt tcc act ggt gac gcg gcc cag ccg gcc agg cgc gcc gta cga agc         96
Gly Ser Thr Gly Asp Ala Ala Gln Pro Ala Arg Arg Ala Val Arg Ser
                20                  25                  30 tta gac att gtg atg act cag tct cca tct tcc ctt tct gtg tca gca        144
Leu Asp Ile Val Met Thr Gln Ser Pro Ser Ser Leu Ser Val Ser Ala
            35                  40                  45 ggt aag aag gtc acc att agt tgc acg gcc agt gag agc ctt tat tca        192
Gly Lys Lys Val Thr Ile Ser Cys Thr Ala Ser Glu Ser Leu Tyr Ser
        50                  55                  60 agc aaa cac aag gtg cac tac ttg gct tgg tac cag aag aaa cca gag        240
Ser Lys His Lys Val His Tyr Leu Ala Trp Tyr Gln Lys Lys Pro Glu
65                  70                  75                  80 caa tct cct aaa ctg ctg ata tac ggg gca tcc aac cga tac att ggg        288
Gln Ser Pro Lys Leu Leu Ile Tyr Gly Ala Ser Asn Arg Tyr Ile Gly
                85                  90                  95 gtc cct gat cgc ttc aca ggc agt gga tct ggg aca gat ttc act ctg        336
Val Pro Asp Arg Phe Thr Gly Ser Gly Ser Gly Thr Asp Phe Thr Leu
                100                 105                 110 acc atc agc agt gta cag gtt gaa gac ctc aca cat tat tac tgt gca        384
Thr Ile Ser Ser Val Gln Val Glu Asp Leu Thr His Tyr Tyr Cys Ala
            115                 120                 125 cag ttt tac agc tat ccg ctc acg ttc ggt gct ggg acc aag ctg gaa        432
Gln Phe Tyr Ser Tyr Pro Leu Thr Phe Gly Ala Gly Thr Lys Leu Glu
        130                 135                 140 atc aaa ggt ggt gga gga tca ggt gga ggt ggt tca gga ggt ggc gga        480
Ile Lys Gly Gly Gly Gly Ser Gly Gly Gly Gly Ser Gly Gly Gly Gly
145                 150                 155                 160 tcc gag gtg aag ctg gtg gag tct gga gga ggc ttg gta cag cct ggg        528
Ser Glu Val Lys Leu Val Glu Ser Gly Gly Gly Leu Val Gln Pro Gly
                165                 170                 175 ggt tct ctg aga ctc tcc tgt gca act tct ggg ttc acc ttc agt gat        576
Gly Ser Leu Arg Leu Ser Cys Ala Thr Ser Gly Phe Thr Phe Ser Asp
                180                 185                 190 ttc tac atg gag tgg gtc cgc cag gct cca ggg aag aga ctg gag tgg        624
Phe Tyr Met Glu Trp Val Arg Gln Ala Pro Gly Lys Arg Leu Glu Trp
            195                 200                 205
```

```
att gct gca agt aga aac aaa gct aat gat tat aca aca gag tac gct      672
Ile Ala Ala Ser Arg Asn Lys Ala Asn Asp Tyr Thr Thr Glu Tyr Ala
    210                 215                 220 gac tct gtg aag ggt cgg ttc atc gtc tcc aga gac act tcc caa agc      720
Asp Ser Val Lys Gly Arg Phe Ile Val Ser Arg Asp Thr Ser Gln Ser
225                 230                 235                 240 atc ctc tac ctt cag atg aat gcc ctg aga gcc gag gac act gcc att      768
Ile Leu Tyr Leu Gln Met Asn Ala Leu Arg Ala Glu Asp Thr Ala Ile
                245                 250                 255 tat tac tgt gca aga gat tac tac ggt agt agc tac tgg tac ttc gat      816
Tyr Tyr Cys Ala Arg Asp Tyr Tyr Gly Ser Ser Tyr Trp Tyr Phe Asp
            260                 265                 270 gtc tgg ggc gca ggg acc acg gtc acc gtc tcc tct cga gga ggg ccc      864
Val Trp Gly Ala Gly Thr Thr Val Thr Val Ser Ser Arg Gly Gly Pro
        275                 280                 285 gaa caa aaa ctc atc tca gaa gag gat ctg aat agc gcc gtc gac cat      912
Glu Gln Lys Leu Ile Ser Glu Glu Asp Leu Asn Ser Ala Val Asp His
    290                 295                 300 cat cat cat cat cat tga                                              930
His His His His His
305
```

<210> SEQ ID NO 2
<211> LENGTH: 309
<212> TYPE: PRT
<213> ORGANISM: Artificial Sequence
<220> FEATURE:
<223> OTHER INFORMATION: Synthetic Construct

<400> SEQUENCE: 2

```
Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Val Arg Ser
            20                  25                  30

Leu Asp Ile Val Met Thr Gln Ser Pro Ser Ser Leu Ser Val Ser Ala
        35                  40                  45

Gly Lys Lys Val Thr Ile Ser Cys Thr Ala Ser Glu Ser Leu Tyr Ser
50                  55                  60

Ser Lys His Lys Val His Tyr Leu Ala Trp Tyr Gln Lys Lys Pro Glu
65                  70                  75                  80

Gln Ser Pro Lys Leu Leu Ile Tyr Gly Ala Ser Asn Arg Tyr Ile Gly
                85                  90                  95

Val Pro Asp Arg Phe Thr Gly Ser Gly Ser Gly Thr Asp Phe Thr Leu
            100                 105                 110

Thr Ile Ser Ser Val Gln Val Glu Asp Leu Thr His Tyr Tyr Cys Ala
        115                 120                 125

Gln Phe Tyr Ser Tyr Pro Leu Thr Phe Gly Ala Gly Thr Lys Leu Glu
    130                 135                 140

Ile Lys Gly Gly Gly Gly Ser Gly Gly Gly Gly Ser Gly Gly Gly Gly
145                 150                 155                 160

Ser Glu Val Lys Leu Val Glu Ser Gly Gly Gly Leu Val Gln Pro Gly
                165                 170                 175

Gly Ser Leu Arg Leu Ser Cys Ala Thr Ser Gly Phe Thr Phe Ser Asp
            180                 185                 190

Phe Tyr Met Glu Trp Val Arg Gln Ala Pro Gly Lys Arg Leu Glu Trp
        195                 200                 205

Ile Ala Ala Ser Arg Asn Lys Ala Asn Asp Tyr Thr Thr Glu Tyr Ala
```

```
                    210               215                  220
Asp Ser Val Lys Gly Arg Phe Ile Val Ser Arg Asp Thr Ser Gln Ser
225                 230                  235                 240

Ile Leu Tyr Leu Gln Met Asn Ala Leu Arg Ala Glu Asp Thr Ala Ile
                    245                  250                 255

Tyr Tyr Cys Ala Arg Asp Tyr Tyr Gly Ser Ser Tyr Trp Tyr Phe Asp
                260                  265                 270

Val Trp Gly Ala Gly Thr Thr Val Thr Val Ser Ser Arg Gly Gly Pro
            275                 280                  285

Glu Gln Lys Leu Ile Ser Glu Glu Asp Leu Asn Ser Ala Val Asp His
            290                 295                  300

His His His His His
305

<210> SEQ ID NO 3
<211> LENGTH: 1554
<212> TYPE: DNA
<213> ORGANISM: Artificial Sequence
<220> FEATURE:
<223> OTHER INFORMATION: Humanized E06 single-chain antibody with
      IgG1-Fc (E06scFv-Fc)
<220> FEATURE:
<221> NAME/KEY: CDS
<222> LOCATION: (1)..(1554)

<400> SEQUENCE: 3
```

| | | | | | | | | | | | | | | | | |
|---|---|---|---|---|---|---|---|---|---|---|---|---|---|---|---|---|
| atg | gag | acc | gac | aca | ctg | ttg | ttg | tgg | gtg | ttg | ctc | ctc | tgg | gtg | cca | 48 |
| Met | Glu | Thr | Asp | Thr | Leu | Leu | Leu | Trp | Val | Leu | Leu | Leu | Trp | Val | Pro | |
| 1 | | | | 5 | | | | | 10 | | | | | 15 | | |
| gga | agc | aca | ggt | gac | gct | gct | gac | atc | gtc | atg | acc | cag | agc | ccc | gac | 96 |
| Gly | Ser | Thr | Gly | Asp | Ala | Ala | Asp | Ile | Val | Met | Thr | Gln | Ser | Pro | Asp | |
| | | | 20 | | | | | 25 | | | | | 30 | | | |
| tct | ctc | gcg | gtt | tct | ctg | gga | gag | cgg | gca | aca | atc | aac | tgc | aca | gca | 144 |
| Ser | Leu | Ala | Val | Ser | Leu | Gly | Glu | Arg | Ala | Thr | Ile | Asn | Cys | Thr | Ala | |
| | | 35 | | | | | 40 | | | | | 45 | | | | |
| agc | gaa | tcc | ctg | tac | tca | tcc | aag | cac | gtg | cat | tac | ctc | gct | tgg | tac | 192 |
| Ser | Glu | Ser | Leu | Tyr | Ser | Ser | Lys | His | Val | His | Tyr | Leu | Ala | Trp | Tyr | |
| | 50 | | | | | 55 | | | | | 60 | | | | | |
| cag | cag | aaa | cca | ggg | caa | cca | cca | aag | ctc | ctc | att | tat | ggg | gcc | agc | 240 |
| Gln | Gln | Lys | Pro | Gly | Gln | Pro | Pro | Lys | Leu | Leu | Ile | Tyr | Gly | Ala | Ser | |
| 65 | | | | 70 | | | | | 75 | | | | | 80 | | |
| aac | aga | tat | att | gga | gtc | cca | gat | cga | ttc | agc | ggt | tcc | ggc | tcc | gga | 288 |
| Asn | Arg | Tyr | Ile | Gly | Val | Pro | Asp | Arg | Phe | Ser | Gly | Ser | Gly | Ser | Gly | |
| | | | 85 | | | | | 90 | | | | | 95 | | | |
| aca | gac | ttt | acc | ctc | acg | ata | agc | agc | ctg | cag | gcg | gaa | gat | gtg | gcc | 336 |
| Thr | Asp | Phe | Thr | Leu | Thr | Ile | Ser | Ser | Leu | Gln | Ala | Glu | Asp | Val | Ala | |
| | | | 100 | | | | | 105 | | | | | 110 | | | |
| gtg | tat | tac | tgc | gca | caa | ttc | tac | agc | tat | cct | ctg | acc | ttc | gga | gga | 384 |
| Val | Tyr | Tyr | Cys | Ala | Gln | Phe | Tyr | Ser | Tyr | Pro | Leu | Thr | Phe | Gly | Gly | |
| | | 115 | | | | | 120 | | | | | 125 | | | | |
| gga | aca | aaa | gtg | gag | atc | aaa | ggc | gga | ggt | gga | tcc | gga | ggg | ggt | gga | 432 |
| Gly | Thr | Lys | Val | Glu | Ile | Lys | Gly | Gly | Gly | Gly | Ser | Gly | Gly | Gly | Gly | |
| | 130 | | | | | 135 | | | | | 140 | | | | | |
| tct | gga | ggt | ggc | ggt | agt | gaa | gtg | cag | ctg | gtg | gaa | agt | gga | ggc | ggc | 480 |
| Ser | Gly | Gly | Gly | Gly | Ser | Glu | Val | Gln | Leu | Val | Glu | Ser | Gly | Gly | Gly | |
| 145 | | | | 150 | | | | | 155 | | | | | 160 | | |
| ctg | gtg | caa | cca | ggt | ggc | tct | ctg | agg | ctg | tca | tgc | gct | gcc | tct | gga | 528 |
| Leu | Val | Gln | Pro | Gly | Gly | Ser | Leu | Arg | Leu | Ser | Cys | Ala | Ala | Ser | Gly | |
| | | | 165 | | | | | 170 | | | | | 175 | | | |
| ttt | acc | ttc | tca | gat | ttc | tac | atg | gaa | tgg | gtc | aga | caa | gcc | cct | gga | 576 |

```
                Phe Thr Phe Ser Asp Phe Tyr Met Glu Trp Val Arg Gln Ala Pro Gly
                                180                 185                 190 aag ggg ctc gag tgg gtg gcc gct tcc agg aac aag gct aat gac tac          624
Lys Gly Leu Glu Trp Val Ala Ala Ser Arg Asn Lys Ala Asn Asp Tyr
            195                 200                 205 acc aca gag tac gcc gca agt gtt aaa ggc cgc ttt ata atc tcc cgc          672
Thr Thr Glu Tyr Ala Ala Ser Val Lys Gly Arg Phe Ile Ile Ser Arg
    210                 215                 220 gat gac tct aag aac tcc ttg tac ctt caa atg aat agt ctc aag aca          720
Asp Asp Ser Lys Asn Ser Leu Tyr Leu Gln Met Asn Ser Leu Lys Thr
225                 230                 235                 240 gaa gat aca gcg gta tac tac tgc gcc cgc gac tac tac gga tca agt          768
Glu Asp Thr Ala Val Tyr Tyr Cys Ala Arg Asp Tyr Tyr Gly Ser Ser
                245                 250                 255 tat tgg tac ttc gat gtt tgg aga gct ggc aca ctt gtg act gtc agc          816
Tyr Trp Tyr Phe Asp Val Trp Arg Ala Gly Thr Leu Val Thr Val Ser
            260                 265                 270 agt ctt gat cct aaa tcc tct gac aag acc tat acc tgc cca cct tgt          864
Ser Leu Asp Pro Lys Ser Ser Asp Lys Thr Tyr Thr Cys Pro Pro Cys
    275                 280                 285 ccc gcc cca gaa ctt ctg ggt ggc cca tcc gtg ttt ctg ttc cca cca          912
Pro Ala Pro Glu Leu Leu Gly Gly Pro Ser Val Phe Leu Phe Pro Pro
290                 295                 300 aag cca aag gat aca ctc atg atc tct cgc act ccg gaa gtc acg tgc          960
Lys Pro Lys Asp Thr Leu Met Ile Ser Arg Thr Pro Glu Val Thr Cys
305                 310                 315                 320 gtc gtg gtt gat gtg tca cac gag gac ccg gag gtc aaa ttc aat tgg         1008
Val Val Val Asp Val Ser His Glu Asp Pro Glu Val Lys Phe Asn Trp
                325                 330                 335 tac gtg gac gga gtc gag gtg cac aac gcc aag aca aag cca cgc gaa         1056
Tyr Val Asp Gly Val Glu Val His Asn Ala Lys Thr Lys Pro Arg Glu
            340                 345                 350 gag cag tac aac agc acg tat aga gta gtg agc gtg ctg aca gtg ctc         1104
Glu Gln Tyr Asn Ser Thr Tyr Arg Val Val Ser Val Leu Thr Val Leu
    355                 360                 365 cac cag gat tgg ctt aac ggt aag gaa tac aag tgt aag gtc tcc aac         1152
His Gln Asp Trp Leu Asn Gly Lys Glu Tyr Lys Cys Lys Val Ser Asn
370                 375                 380 aaa gct ctt cct gct cca ata gaa aag acc att tca aag gcc aag ggg         1200
Lys Ala Leu Pro Ala Pro Ile Glu Lys Thr Ile Ser Lys Ala Lys Gly
385                 390                 395                 400 caa cct cga gaa ccc cag gtg tac acg ctg cct ccc agc cga gag gag         1248
Gln Pro Arg Glu Pro Gln Val Tyr Thr Leu Pro Pro Ser Arg Glu Glu
                405                 410                 415 atg acc aag aac caa gta agt ctg aca tgc ctt gtc aaa ggg ttc tac         1296
Met Thr Lys Asn Gln Val Ser Leu Thr Cys Leu Val Lys Gly Phe Tyr
            420                 425                 430 ccc tca gac atc gcc gtg gaa tgg gaa agc aac ggt caa ccc gaa aac         1344
Pro Ser Asp Ile Ala Val Glu Trp Glu Ser Asn Gly Gln Pro Glu Asn
    435                 440                 445 aat tac aag aca acg cca ccg gta ctc gat tcc gat ggt tcc ttt ttt         1392
Asn Tyr Lys Thr Thr Pro Pro Val Leu Asp Ser Asp Gly Ser Phe Phe
450                 455                 460 ctg tac tcc aaa ctc acg gtg gac aag agt cga tgg cag cag gga aac         1440
Leu Tyr Ser Lys Leu Thr Val Asp Lys Ser Arg Trp Gln Gln Gly Asn
465                 470                 475                 480 gtt ttc tcc tgt tcc gtg atg cac gaa gca ctg cac aat cac tat acc         1488
Val Phe Ser Cys Ser Val Met His Glu Ala Leu His Asn His Tyr Thr
                485                 490                 495
```

-continued

```
cag aag tca ctg agt ttg agc cct ggc aaa gga ggg ggc gga tca cat    1536
Gln Lys Ser Leu Ser Leu Ser Pro Gly Lys Gly Gly Gly Gly Ser His
            500                 505                 510 cat cac cat cac cat taa                                             1554
His His His His His
        515
```

<210> SEQ ID NO 4
<211> LENGTH: 517
<212> TYPE: PRT
<213> ORGANISM: Artificial Sequence
<220> FEATURE:
<223> OTHER INFORMATION: Synthetic Construct

<400> SEQUENCE: 4

```
Met Glu Thr Asp Thr Leu Leu Leu Trp Val Leu Leu Leu Trp Val Pro
1               5                   10                  15

Gly Ser Thr Gly Asp Ala Ala Asp Ile Val Met Thr Gln Ser Pro Asp
            20                  25                  30

Ser Leu Ala Val Ser Leu Gly Glu Arg Ala Thr Ile Asn Cys Thr Ala
        35                  40                  45

Ser Glu Ser Leu Tyr Ser Ser Lys His Val His Tyr Leu Ala Trp Tyr
    50                  55                  60

Gln Gln Lys Pro Gly Gln Pro Pro Lys Leu Leu Ile Tyr Gly Ala Ser
65                  70                  75                  80

Asn Arg Tyr Ile Gly Val Pro Asp Arg Phe Ser Gly Ser Gly Ser Gly
                85                  90                  95

Thr Asp Phe Thr Leu Thr Ile Ser Ser Leu Gln Ala Glu Asp Val Ala
            100                 105                 110

Val Tyr Tyr Cys Ala Gln Phe Tyr Ser Tyr Pro Leu Thr Phe Gly Gly
        115                 120                 125

Gly Thr Lys Val Glu Ile Lys Gly Gly Gly Gly Ser Gly Gly Gly Gly
    130                 135                 140

Ser Gly Gly Gly Gly Ser Glu Val Gln Leu Val Glu Ser Gly Gly Gly
145                 150                 155                 160

Leu Val Gln Pro Gly Gly Ser Leu Arg Leu Ser Cys Ala Ala Ser Gly
                165                 170                 175

Phe Thr Phe Ser Asp Phe Tyr Met Glu Trp Val Arg Gln Ala Pro Gly
            180                 185                 190

Lys Gly Leu Glu Trp Val Ala Ala Ser Arg Asn Lys Ala Asn Asp Tyr
        195                 200                 205

Thr Thr Glu Tyr Ala Ala Ser Val Lys Gly Arg Phe Ile Ile Ser Arg
    210                 215                 220

Asp Asp Ser Lys Asn Ser Leu Tyr Leu Gln Met Asn Ser Leu Lys Thr
225                 230                 235                 240

Glu Asp Thr Ala Val Tyr Tyr Cys Ala Arg Asp Tyr Tyr Gly Ser Ser
                245                 250                 255

Tyr Trp Tyr Phe Asp Val Trp Arg Ala Gly Thr Leu Val Thr Val Ser
            260                 265                 270

Ser Leu Asp Pro Lys Ser Ser Asp Lys Thr Tyr Thr Cys Pro Pro Cys
        275                 280                 285

Pro Ala Pro Glu Leu Leu Gly Gly Pro Ser Val Phe Leu Phe Pro Pro
    290                 295                 300

Lys Pro Lys Asp Thr Leu Met Ile Ser Arg Thr Pro Glu Val Thr Cys
305                 310                 315                 320

Val Val Val Asp Val Ser His Glu Asp Pro Glu Val Lys Phe Asn Trp
```

```
                    325                 330                 335
Tyr Val Asp Gly Val Glu Val His Asn Ala Lys Thr Lys Pro Arg Glu
                340                 345                 350

Glu Gln Tyr Asn Ser Thr Tyr Arg Val Val Ser Val Leu Thr Val Leu
            355                 360                 365

His Gln Asp Trp Leu Asn Gly Lys Glu Tyr Lys Cys Lys Val Ser Asn
370                 375                 380

Lys Ala Leu Pro Ala Pro Ile Glu Lys Thr Ile Ser Lys Ala Lys Gly
385                 390                 395                 400

Gln Pro Arg Glu Pro Gln Val Tyr Thr Leu Pro Pro Ser Arg Glu Glu
                405                 410                 415

Met Thr Lys Asn Gln Val Ser Leu Thr Cys Leu Val Lys Gly Phe Tyr
            420                 425                 430

Pro Ser Asp Ile Ala Val Glu Trp Glu Ser Asn Gly Gln Pro Glu Asn
        435                 440                 445

Asn Tyr Lys Thr Thr Pro Pro Val Leu Asp Ser Asp Gly Ser Phe Phe
    450                 455                 460

Leu Tyr Ser Lys Leu Thr Val Asp Lys Ser Arg Trp Gln Gln Gly Asn
465                 470                 475                 480

Val Phe Ser Cys Ser Val Met His Glu Ala Leu His Asn His Tyr Thr
                485                 490                 495

Gln Lys Ser Leu Ser Leu Ser Pro Gly Lys Gly Gly Gly Ser His
            500                 505                 510

His His His His His
        515

<210> SEQ ID NO 5
<211> LENGTH: 5
<212> TYPE: PRT
<213> ORGANISM: Artificial Sequence
<220> FEATURE:
<223> OTHER INFORMATION: Peptide Linker

<400> SEQUENCE: 5

Gly Gly Gly Gly Ser
1               5

<210> SEQ ID NO 6
<211> LENGTH: 7
<212> TYPE: PRT
<213> ORGANISM: Artificial Sequence
<220> FEATURE:
<223> OTHER INFORMATION: VH CDR1

<400> SEQUENCE: 6

Gly Phe Thr Phe Ser Asp Phe
1               5

<210> SEQ ID NO 7
<211> LENGTH: 8
<212> TYPE: PRT
<213> ORGANISM: Artificial Sequence
<220> FEATURE:
<223> OTHER INFORMATION: VH CDR2

<400> SEQUENCE: 7

Arg Asn Lys Ala Asn Asp Tyr Thr
1               5

<210> SEQ ID NO 8
```

```
<211> LENGTH: 16
<212> TYPE: PRT
<213> ORGANISM: Artificial Sequence
<220> FEATURE:
<223> OTHER INFORMATION: VH CDR3

<400> SEQUENCE: 8

Cys Ala Arg Asp Tyr Tyr Gly Ser Ser Tyr Trp Tyr Phe Asp Val Trp
1               5                   10                  15

<210> SEQ ID NO 9
<211> LENGTH: 17
<212> TYPE: PRT
<213> ORGANISM: Artificial Sequence
<220> FEATURE:
<223> OTHER INFORMATION: VL CDR1

<400> SEQUENCE: 9

Thr Ala Ser Glu Ser Leu Tyr Ser Ser Lys His Lys Val His Tyr Leu
1               5                   10                  15

Ala

<210> SEQ ID NO 10
<211> LENGTH: 7
<212> TYPE: PRT
<213> ORGANISM: Artificial Sequence
<220> FEATURE:
<223> OTHER INFORMATION: VL CDR2

<400> SEQUENCE: 10

Gly Ala Ser Asn Arg Tyr Ile
1               5

<210> SEQ ID NO 11
<211> LENGTH: 10
<212> TYPE: PRT
<213> ORGANISM: Artificial Sequence
<220> FEATURE:
<223> OTHER INFORMATION: VL CDR3

<400> SEQUENCE: 11

Cys Ala Gln Phe Tyr Ser Tyr Pro Leu Thr
1               5                   10

<210> SEQ ID NO 12
<211> LENGTH: 16
<212> TYPE: PRT
<213> ORGANISM: Artificial Sequence
<220> FEATURE:
<223> OTHER INFORMATION: VL CDR1-humanized

<400> SEQUENCE: 12

Thr Ala Ser Glu Ser Leu Tyr Ser Ser Lys His Val His Tyr Leu Ala
1               5                   10                  15

<210> SEQ ID NO 13
<211> LENGTH: 1587
<212> TYPE: DNA
<213> ORGANISM: Artificial Sequence
<220> FEATURE:
<223> OTHER INFORMATION: Chimeric E06scFv-human IgG1-Fc antibody
      sequence
<220> FEATURE:
<221> NAME/KEY: CDS
<222> LOCATION: (1)..(1587)

<400> SEQUENCE: 13
```

-continued

| | | |
|---|---|---|
| atg gag aca gac aca ctc ctg cta tgg gta ctg ctg ctc tgg gtt cca<br>Met Glu Thr Asp Thr Leu Leu Leu Trp Val Leu Leu Leu Trp Val Pro<br>1                       5                           10                       15 | 48 | |
| ggt tcc act ggt gac gcg gcc cag ccg gcc agg cgc gcc gta cga agc<br>Gly Ser Thr Gly Asp Ala Ala Gln Pro Ala Arg Arg Ala Val Arg Ser<br>                    20                       25                       30 | 96 | |
| tta gac att gtg atg act cag tct cca tct tcc ctt tct gtg tca gca<br>Leu Asp Ile Val Met Thr Gln Ser Pro Ser Ser Leu Ser Val Ser Ala<br>          35                       40                       45 | 144 | |
| ggt aag aag gtc acc att agt tgc acg gcc agt gag agc ctt tat tca<br>Gly Lys Lys Val Thr Ile Ser Cys Thr Ala Ser Glu Ser Leu Tyr Ser<br>50                            55                       60 | 192 | |
| agc aaa cac aag gtg cac tac ttg gct tgg tac cag aag aaa cca gag<br>Ser Lys His Lys Val His Tyr Leu Ala Trp Tyr Gln Lys Lys Pro Glu<br>65                       70                       75                       80 | 240 | |
| caa tct cct aaa ctg ctg ata tac ggg gca tcc aac cga tac att ggg<br>Gln Ser Pro Lys Leu Leu Ile Tyr Gly Ala Ser Asn Arg Tyr Ile Gly<br>                    85                       90                       95 | 288 | |
| gtc cct gat cgc ttc aca ggc agt gga tct ggg aca gat ttc act ctg<br>Val Pro Asp Arg Phe Thr Gly Ser Gly Ser Gly Thr Asp Phe Thr Leu<br>                100                      105                      110 | 336 | |
| acc atc agc agt gta cag gtt gaa gac ctc aca cat tat tac tgt gca<br>Thr Ile Ser Ser Val Gln Val Glu Asp Leu Thr His Tyr Tyr Cys Ala<br>            115                      120                      125 | 384 | |
| cag ttt tac agc tat ccg ctc acg ttc ggt gct ggg acc aag ctg gaa<br>Gln Phe Tyr Ser Tyr Pro Leu Thr Phe Gly Ala Gly Thr Lys Leu Glu<br>130                          135                      140 | 432 | |
| atc aaa ggt ggt gga gga tca ggt gga ggt ggt tca gga ggt ggc gga<br>Ile Lys Gly Gly Gly Gly Ser Gly Gly Gly Gly Ser Gly Gly Gly Gly<br>145                          150                          155                       160 | 480 | |
| tcc gag gtg aag ctg gtg gag tct gga gga ggc ttg gta cag cct ggg<br>Ser Glu Val Lys Leu Val Glu Ser Gly Gly Gly Leu Val Gln Pro Gly<br>                165                      170                      175 | 528 | |
| ggt tct ctg aga ctc tcc tgt gca act tct ggg ttc acc ttc agt gat<br>Gly Ser Leu Arg Leu Ser Cys Ala Thr Ser Gly Phe Thr Phe Ser Asp<br>            180                      185                      190 | 576 | |
| ttc tac atg gag tgg gtc cgc cag gct cca ggg aag aga ctg gag tgg<br>Phe Tyr Met Glu Trp Val Arg Gln Ala Pro Gly Lys Arg Leu Glu Trp<br>                195                      200                      205 | 624 | |
| att gct gca agt aga aac aaa gct aat gat tat aca aca gag tac gct<br>Ile Ala Ala Ser Arg Asn Lys Ala Asn Asp Tyr Thr Thr Glu Tyr Ala<br>210                          215                      220 | 672 | |
| gac tct gtg aag ggt cgg ttc atc gtc tcc aga gac act tcc caa agc<br>Asp Ser Val Lys Gly Arg Phe Ile Val Ser Arg Asp Thr Ser Gln Ser<br>225                          230                          235                       240 | 720 | |
| atc ctc tac ctt cag atg aat gcc ctg aga gcc gag gac act gcc att<br>Ile Leu Tyr Leu Gln Met Asn Ala Leu Arg Ala Glu Asp Thr Ala Ile<br>                245                      250                      255 | 768 | |
| tat tac tgt gca aga gat tac tac ggt agt agc tac tgg tac ttc gat<br>Tyr Tyr Cys Ala Arg Asp Tyr Tyr Gly Ser Ser Tyr Trp Tyr Phe Asp<br>            260                      265                      270 | 816 | |
| gtc tgg ggc gca ggg acc acg gtc acc gtc tcc tct ctg gac ccg aag<br>Val Trp Gly Ala Gly Thr Thr Val Thr Val Ser Ser Leu Asp Pro Lys<br>                275                      280                      285 | 864 | |
| tct tct gac aaa act tac aca tgc cca ccg tgc cca gca cct gaa ctc<br>Ser Ser Asp Lys Thr Tyr Thr Cys Pro Pro Cys Pro Ala Pro Glu Leu<br>290                          295                      300 | 912 | |
| ctg ggg gga ccg tca gtc ttc ctc ttc ccc cca aaa ccc aag gac acc<br>Leu Gly Gly Pro Ser Val Phe Leu Phe Pro Pro Lys Pro Lys Asp Thr<br>305                          310                      315                      320 | 960 | |

```
ctc atg atc tcc cgg acc cct gag gtc aca tgc gtg gtg gtg gac gtg     1008
Leu Met Ile Ser Arg Thr Pro Glu Val Thr Cys Val Val Val Asp Val
            325                 330                 335 agc cac gaa gac cct gag gtc aag ttc aac tgg tac gtg gac ggc gtg     1056
Ser His Glu Asp Pro Glu Val Lys Phe Asn Trp Tyr Val Asp Gly Val
            340                 345                 350 gag gtg cat aat gcc aag aca aag ccg cgg gag gag cag tac aac agc     1104
Glu Val His Asn Ala Lys Thr Lys Pro Arg Glu Glu Gln Tyr Asn Ser
            355                 360                 365 acg tac cgt gtg gtc agc gtc ctc acc gtc ctg cac cag gac tgg ctg     1152
Thr Tyr Arg Val Val Ser Val Leu Thr Val Leu His Gln Asp Trp Leu
    370                 375                 380 aat ggc aag gag tac aag tgc aag gtc tcc aac aaa gcc ctc cca gcc     1200
Asn Gly Lys Glu Tyr Lys Cys Lys Val Ser Asn Lys Ala Leu Pro Ala
385                 390                 395                 400 ccc atc gag aaa acc atc tcc aaa gcc aaa ggg cag ccc cga gaa cca     1248
Pro Ile Glu Lys Thr Ile Ser Lys Ala Lys Gly Gln Pro Arg Glu Pro
                405                 410                 415 cag gtg tac acc ctg ccc cca tcc cgg gag gag atg acc aag aac cag     1296
Gln Val Tyr Thr Leu Pro Pro Ser Arg Glu Glu Met Thr Lys Asn Gln
            420                 425                 430 gtc agc ctg acc tgc ctg gtc aaa ggc ttc tat ccc agc gac atc gcc     1344
Val Ser Leu Thr Cys Leu Val Lys Gly Phe Tyr Pro Ser Asp Ile Ala
            435                 440                 445 gtg gag tgg gag agc aat ggg cag ccg gag aac aac tac aag acc acg     1392
Val Glu Trp Glu Ser Asn Gly Gln Pro Glu Asn Asn Tyr Lys Thr Thr
            450                 455                 460 cct ccc gtg ctg gac tcc gac ggc tcc ttc ttc ctc tac agc aag ctc     1440
Pro Pro Val Leu Asp Ser Asp Gly Ser Phe Phe Leu Tyr Ser Lys Leu
465                 470                 475                 480 acc gtg gac aag agc agg tgg cag cag ggg aac gtc ttc tca tgc tcc     1488
Thr Val Asp Lys Ser Arg Trp Gln Gln Gly Asn Val Phe Ser Cys Ser
                485                 490                 495 gtg atg cac gag gct ctg cac aac cac tac acg cag aag agc ctc tcc     1536
Val Met His Glu Ala Leu His Asn His Tyr Thr Gln Lys Ser Leu Ser
            500                 505                 510 ctg tct ccg ggt aaa ggt gga ggt gga tca cat cat cat cat cat cat     1584
Leu Ser Pro Gly Lys Gly Gly Gly Gly Ser His His His His His His
            515                 520                 525 taa                                                                 1587
```

<210> SEQ ID NO 14
<211> LENGTH: 528
<212> TYPE: PRT
<213> ORGANISM: Artificial Sequence
<220> FEATURE:
<223> OTHER INFORMATION: Synthetic Construct

<400> SEQUENCE: 14

```
Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Val Arg Ser
            20                  25                  30

Leu Asp Ile Val Met Thr Gln Ser Pro Ser Ser Leu Ser Val Ser Ala
        35                  40                  45

Gly Lys Lys Val Thr Ile Ser Cys Thr Ala Ser Glu Ser Leu Tyr Ser
    50                  55                  60

Ser Lys His Lys Val His Tyr Leu Ala Trp Tyr Gln Lys Lys Pro Glu
65                  70                  75                  80
```

```
Gln Ser Pro Lys Leu Leu Ile Tyr Gly Ala Ser Asn Arg Tyr Ile Gly
                85                  90                  95
Val Pro Asp Arg Phe Thr Gly Ser Gly Ser Gly Thr Asp Phe Thr Leu
            100                 105                 110
Thr Ile Ser Ser Val Gln Val Glu Asp Leu Thr His Tyr Tyr Cys Ala
        115                 120                 125
Gln Phe Tyr Ser Tyr Pro Leu Thr Phe Gly Ala Gly Thr Lys Leu Glu
    130                 135                 140
Ile Lys Gly Gly Gly Gly Ser Gly Gly Gly Gly Ser Gly Gly Gly Gly
145                 150                 155                 160
Ser Glu Val Lys Leu Val Glu Ser Gly Gly Gly Leu Val Gln Pro Gly
                165                 170                 175
Gly Ser Leu Arg Leu Ser Cys Ala Thr Ser Gly Phe Thr Phe Ser Asp
            180                 185                 190
Phe Tyr Met Glu Trp Val Arg Gln Ala Pro Gly Lys Arg Leu Glu Trp
        195                 200                 205
Ile Ala Ala Ser Arg Asn Lys Ala Asn Asp Tyr Thr Thr Glu Tyr Ala
    210                 215                 220
Asp Ser Val Lys Gly Arg Phe Ile Val Ser Arg Asp Thr Ser Gln Ser
225                 230                 235                 240
Ile Leu Tyr Leu Gln Met Asn Ala Leu Arg Ala Glu Asp Thr Ala Ile
                245                 250                 255
Tyr Tyr Cys Ala Arg Asp Tyr Tyr Gly Ser Ser Tyr Trp Tyr Phe Asp
            260                 265                 270
Val Trp Gly Ala Gly Thr Thr Val Thr Val Ser Ser Leu Asp Pro Lys
        275                 280                 285
Ser Ser Asp Lys Thr Tyr Thr Cys Pro Pro Cys Pro Ala Pro Glu Leu
    290                 295                 300
Leu Gly Gly Pro Ser Val Phe Leu Phe Pro Pro Lys Pro Lys Asp Thr
305                 310                 315                 320
Leu Met Ile Ser Arg Thr Pro Glu Val Thr Cys Val Val Val Asp Val
                325                 330                 335
Ser His Glu Asp Pro Glu Val Lys Phe Asn Trp Tyr Val Asp Gly Val
            340                 345                 350
Glu Val His Asn Ala Lys Thr Lys Pro Arg Glu Glu Gln Tyr Asn Ser
        355                 360                 365
Thr Tyr Arg Val Val Ser Val Leu Thr Val Leu His Gln Asp Trp Leu
    370                 375                 380
Asn Gly Lys Glu Tyr Lys Cys Lys Val Ser Asn Lys Ala Leu Pro Ala
385                 390                 395                 400
Pro Ile Glu Lys Thr Ile Ser Lys Ala Lys Gly Gln Pro Arg Glu Pro
                405                 410                 415
Gln Val Tyr Thr Leu Pro Pro Ser Arg Glu Glu Met Thr Lys Asn Gln
            420                 425                 430
Val Ser Leu Thr Cys Leu Val Lys Gly Phe Tyr Pro Ser Asp Ile Ala
        435                 440                 445
Val Glu Trp Glu Ser Asn Gly Gln Pro Glu Asn Asn Tyr Lys Thr Thr
    450                 455                 460
Pro Pro Val Leu Asp Ser Asp Gly Ser Phe Phe Leu Tyr Ser Lys Leu
465                 470                 475                 480
Thr Val Asp Lys Ser Arg Trp Gln Gln Gly Asn Val Phe Ser Cys Ser
                485                 490                 495
```

```
Val Met His Glu Ala Leu His Asn His Tyr Thr Gln Lys Ser Leu Ser
            500                 505                 510

Leu Ser Pro Gly Lys Gly Gly Gly Gly Ser His His His His His
        515                 520                 525
```

THERAPIES AND METHODS TO TREAT TLR2-MEDIATED DISEASES AND DISORDERS

CROSS REFERENCE TO RELATED APPLICATIONS

This application is a U.S. National Phase application filed under 35 U.S.C. § 371 and claims priority to International Application No. PCT/US2019/015723, filed Jan. 29, 2019, which application claims priority under 35 U.S.C. § 119 from Provisional Application Ser. No. 62/623,276, filed Jan. 29, 2018, the disclosures of which are incorporated herein by reference.

GOVERNMENT LICENSE RIGHTS

This invention was made with Government support under Grant No. HL088093 awarded by the National Institutes of Health. The Government has certain rights in the invention.

TECHNICAL FIELD

The disclosure provides for methods and treatments of TLR2-mediated diseases and disorders comprising administering an antibody, antibody fragment, or polypeptide that binds to and inhibits the biological activity of an oxidized phospholipids.

INCORPORATION BY REFERENCE OF SEQUENCE LISTING

Accompanying this filing is a Sequence Listing entitled "Sequence-Listing_ST25.txt", created on Jan. 29, 2019 and having 34,203 bytes of data, machine formatted on IBM-PC, MS-Windows operating system. The sequence listing is hereby incorporated herein by reference in its entirety for all purposes.

BACKGROUND

Phospholipids containing polyunsaturated fatty acids are highly prone to modification by reactive oxygen species. Such phospholipids tend to undergo lipid peroxidation to form oxidized phospholipids (OxPLs) which induce cytotoxicity and apoptosis and which play a significant role in inflammation. OxPLs have been shows to play a role in interleukin transcription, phenotype switching of smooth muscle cells and apoptotic mechanisms of the modified phospholipids. Thus, peroxidation greatly alters the physiochemical properties of membrane lipid bilayers and consequently induces signaling depending upon the formation or reorganization of membrane domains or molecular binding. Distinct OxPLs species may interact with specific binding sites and receptors leading to the activation of individual signaling pathways.

Human coronary atherosclerosis is a chronic inflammatory disease that occurs due to lipid abnormalities. Pro-inflammatory oxidized low-density lipoprotein (OxLDL) has been suggested to be a link between lipid accumulation and inflammation in vessel walls. Moreoer, increased levels of phospholipids' oxidation products have been detected in different organs and pathological states, including atherosclerotic vessels, inflamed lung, non-alcoholic liver disease, plasma of patients with coronary artery disease, as well as in apoptotic cells, virus-infected cells and cells stimulated with inflammatory agonists. Studies have been done on two HDL-associated enzymes: serum paraoxonase (PON1) and PAF-acetylhydrolase (PAF-AH); both of which are responsible for hydrolysis of plasma oxidized phospholipids thereby providing evidence for their role in atherosclerosis. Another important marker of oxidative stress is the association of OxPLs with the apolipoprotein B-100 particle (OxPLs/apoB) of LDL. Increased levels of OxPLs/apoB are implicated in coronary artery disease, progression of carotid and femoral atherosclerosis and the prediction of cardiovascular events.

SUMMARY

The disclosure provides for methods and treatments of TLR2-mediated diseases and disorders comprising administering an antibody, antibody fragment, or polypeptide that binds to and inhibits the biological activity of an oxidized phospholipid. As shown in the studies presented herein, neutralization of OxPL by the in vivo endogenous expression of the EO6 antibody (using the EO6-scFv transgenic mouse) greatly inhibits atherosclerosis formation caused by TLR2 agonism. Injections of the TLR2 agonist PAM3CSK4 into cholesterol-fed $Ldlr^{-/-}$ mice leads to dramatic enhancement of atherosclerosis. A similar set of injections into the EO6-scFv transgenic mice (on the $Ldlr^{-/-}$ background) resulted in a significant inhibition of lesion formation. In other studies, presented herein, it was shown that neutralization of OxPL can protect against disease progression in a TLR2-driven mouse model of Kawasaki Disease. Administration of the pathogen *Lactobaccilus casei* has been shown to cause Kawasaki-like disease in mice, with resultant enhanced atherosclerosis, coronary artery arteritis and abdominal aneurysms. This is TLR2 dependent, as administering *L. Casei* to TLR-2 deficient mice has no disease causing effect. IL-1 expression has also been strongly associated with Kawasaki Disease. OxPL are also potent inducers of IL-1 release and inflammation. Injection of *L. Casei* into the EO6 transgenic mice (in the $Ldlr^{-/-}$ background) under an identical protocol resulted in dramatic reductions not only in atherosclerosis, but of great relevance, in coronary arteritis as compared to injections into $Ldlr^{-/-}$ mice. The EO6 antibody does not directly bind *L. Casei* and therefore, it presumably neutralizes the inflammatory effects of OxPL caused by the inflammatory effects associated with TLR2 mediated agonism.

The development of coronary arteritis and subsequently coronary aneurysms are a fatal complication in children afflicted with Kawasaki disease, estimated to occur in up to 25% of children despite current therapy, which is mainly treatment with intravenous immune globulin (IVIg) derived from pooled and purified human plasma and aspirin, which is a generalized, non-specific anti-inflammatory therapy. Due to the ability of any anti-OxPL antibodies to decrease inflammatory processes, including the decrease in IL-1B production, as well as its ability to confer protection in the TLR2-mediated mouse model of Kawasaki's disease, injections of humanized or human equivalent anti-OxPL antibody modified to enhance its biological effectiveness might then confer protection against TLR2-associated diseases including Kawasaki disease. Since such anti-OxPL antibodies are present in human B cell repertoire, a targeted, recombinant therapy could confer clinical benefit to such disease without the side effects of immunosuppression or plasma-derived therapies.

The experimental data thus demonstrate that atherosclerosis and inflammatory arteritis caused by TLR2-mediated agonism in vivo in mice can be prevented by neutralization of OxPL. TLR2 agonism has been implicated in numerous bacterial diseases of course, but also in a variety of so-called autoimmune mediated diseases such as lupus, rheumatoid arthritis, and others. In summary, the data demonstrates that neutralization of OxPL by the use of antibodies, antibody fragments or other binding domains targeting the PC of OxPL can ameliorate or prevent many diseases that are accentuated, or caused to worsen in progression, by activation of TLR 2 mediated signaling pathways.

In a certain embodiment, the disclosure provides a method of treating a subject with a toll-like receptor 2 (TLR2)-mediated disease or disorder comprising, administering a therapeutically effective amount of an antibody, antibody fragment, or polypeptide that binds specifically to an oxidative phospholipid (OxPL), wherein the antibody, antibody fragment or polypeptide inhibits a biological activity of the OxPL. In a further embodiment, the method further comprises administering to the subject an additional therapeutic agent that is useful for treating a TLR2-mediated disease or disorder. Examples of TLR2-mediated diseases or disorders, includes but are not limited to, Kawasaki disease, type 2 diabetes, rheumatoid arthritis, dermatologic disease, multiple sclerosis, systemic lupus erythematosus, ulcerative colitis, Graves' Disease, Sjögren's syndrome, autoimmune thyroid diseases, or vasculitis. In a particular embodiment, the TLR2-mediated disease or disorder is Kawasaki disease. In a further embodiment, the method further comprises administering to the subject Intravenous immunoglobulin (IVIG) and/or salicylates. In yet a further embodiment, the subject is a human subject that is less than five years old. In another embodiment, the biological activity of the OxPL comprises activation of CD36-TLR2 apoptosis pathway. In yet another embodiment, the antibody, antibody fragment, or polypeptide is a single-chain variable fragment (ScFv). In a certain embodiment, the antibody or antibody fragment recognizes and binds to a phosphocholine headgroup of an oxidized phospholipid, wherein the antibody or antibody fragment comprises a variable heavy chain ($V_H$) domain and/or a variable light chain ($V_L$) domain, and wherein (a) the $V_H$ domain comprises an amino acid sequence that includes one, two or three complementarity determining regions (CDRs) selected from the group consisting of: SEQ ID NO:6 and sequence that are at least 95%, 96%, 97%, 98%, 99% or 99.9% identical to SEQ ID NO:6; SEQ ID NO:7 and sequence that are at least 95%, 96%, 97%, 98%, 99% or 99.9% identical to SEQ ID NO:7; and SEQ ID NO:8 and sequence that are at least 95%, 96%, 97%, 98%, 99% or 99.9% identical to SEQ ID NO:8; and (b) the $V_L$ domain comprises an amino acid sequence that includes one, two or three complementarity determining regions (CDRs) selected from the group consisting of: SEQ ID NO:9 or 12 and sequence that are at least 95%, 96%, 97%, 98%, 99% or 99.9% identical to SEQ ID NO:9 or 12; SEQ ID NO:10 and sequence that are at least 95%, 96%, 97%, 98%, 99% or 99.9% identical to SEQ ID NO:10; and SEQ ID NO:11 and sequence that are at least 95%, 96%, 97%, 98%, 99% or 99.9% identical to SEQ ID NO:11. In a further embodiment, the antibody, antibody fragment or polypeptide is administered intravascularly. In yet a further embodiment, the $V_H$ domain comprises an amino acid sequence that includes CDRs comprising SEQ ID NO:6, 7 and 8, and/or the $V_L$ domain comprises an amino acid sequence that includes CDRs comprising SEQ ID NO:9, 10 and 11, or SEQ ID NO:10, 11 and 12. In another embodiment, the antibody or antibody fragment is selected from the group consisting of: (a) an antibody or scFv with heavy and light chain domains comprising the complementarity determining regions of SEQ ID NO:6, 7, 8, 9, 10 and 11; and (b) an antibody or scFv with heavy and light chain domains comprising the complementarity determining regions of SEQ ID NO:6, 7, 8, 10, 11 and 12. In another embodiment, the heavy and light chain domains are linked to an Fc or FC2 region. In yet another embodiment, the antibody fragment comprises a single chain variable fragment ("scFv") that recognizes a phosphocholine headgroup of an oxidized phospholipid. In a particular embodiment, the scFv is soluble under physiological conditions. Other OxPL binding agents that inhibit the biological activity of OxPL can be used (see, e.g., International Publ. No. WO/2013/020995, which is incorporated herein by reference for all purposes).

DESCRIPTION OF DRAWINGS

FIG. 2 shows the nucleotide (SEQ ID NO:1) and amino acid (SEQ ID NO:2) sequence and annotations of the scFv.

FIG. 3 diagrams an in vivo mice model for studying the functions of scFv of the disclosure in pro-inflammatory and high-fat cholesterol diet fed mice when the mice are exposed to an exogenous agonist of Toll-like receptor (TLR2), Pam3CSK$_4$ (PAM3).

FIG. 4A-C shows the effects on the intake and body mass of mice using the in vivo model described in FIG. 3. (A) No significant difference was observed in the intake of food by Ldlr$^{-/-}$ mice vs. Ldlr$^{-/-}$ EO6scFv$^{+/+}$ mice when treated with vehicle. (B) When the mice were treated with Pam3, Ldlr$^{-/-}$ mice had less intake of food in comparison to Ldlr$^{-/-}$ EO6scFv$^{+/+}$ mice. (C) At 12 weeks, the body mass of Ldlr$^{-/-}$ EO6scFv$^{+/+}$ mice was significantly higher than Ldlr$^{-/-}$ mice. No significant differences in body mass were seen between the Ldlr$^{-/-}$ EO6scFv$^{+/+}$ mice and Ldlr$^{-/-}$ mice when treated with vehicle at week 12.

FIG. 6A-B demonstrates that there were no significant differences in (A) lipoprotein cholesterol profile, or (B) lipoprotein triglycerides profile in blood plasma of Ldlr$^{-/-}$ EO6 scFv$^{+/+}$ mice vs. Ldlr$^{-/-}$ mice, e.g., lipoprotein levels were similar in both mice.

FIG. 7A-E indicates that there was less measurable atherosclerosis in Ldlr$^{-/-}$ EO6 scFv$^{+/+}$ mice vs. Ldlr$^{-/-}$ mice. (A) The extent of total aortic atherosclerosis was greater in Ldlr$^{-/-}$ mice vs. Ldlr$^{-/-}$ EO6 scFv$^{+/+}$ mice. (B) There was especially a greater extent of atherosclerosis in the abdominal aorta (below the diaphragm) in the Ldlr$^{-/-}$ mice vs. Ldlr$^{-/-}$ EO6 scFv$^{+/+}$ mice. (C) Figures (A) and (B) above represent two-dimensional analysis by planimimetry of the extent of atherosclerosis. The actual weight of dissected and cleaned aortas are a better integration of total atherosclerosis as it contains a dimension of thickness. The weight of aortas from Ldlr$^{-/-}$ mice were significantly higher than the aortas from Ldlr$^{-/-}$ EO6 scFv$^{+/+}$ mice. (D) When controlled for body mass, the aorta per body mass from Ldlr$^{-/-}$ mice was significantly higher than the aorta per body mass from Ldlr$^{-/-}$ EO6 scFv$^{+/+}$ mice. (E) The extent of atherosclerosis at the aortic root was not different between the two groups.

FIG. 8A-H provides the results of quantitative PCR (qPCR) looking at inflammatory gene expression in adipose tissue of Ldlr$^{-/-}$ EO6scFv$^{+/+}$ mice vs. Ldlr$^{-/-}$ mice. In particular, the expression of (A) IL1b, (B) IL6, (C) TNFα, (E) MCP1, (F) MIP1α, (G) MIP1β, and (H) IL10 were generally lower for Ldlr$^{-/-}$ EO6scFv$^{+/+}$ mice vs. Ldlr$^{-/-}$ mice, whereas IL12 was slightly higher (D).

FIG. 9A-G provides the results of enzyme-linked immunosorbent assays (ELISAs) looking at measured cytokine levels in adipose tissue extracts of Ldlr$^{-/-}$ EO6scFv$^{+/+}$ mice vs. Ldlr$^{-/-}$ mice. In particular, the measured cytokine levels of (A) IL1b, (B) IL6, (C) TNFα, (D) MCP1, (E) MIP1α, (F) MIP1β, and (G) IL10 mirrored the gene expression results presented in FIG. 8.

FIG. 10A-H shows that bone marrow derived cells from Ldlr$^{-/-}$ EO6scFv$^{+/+}$ when differentiated to macrophage M1 or M2 cells and stimulated with PAM3 showed less expression of (A) IL1β, (B) IL6, (C) IL12, (D) TNFα, (E) MCP1, (F) MIP1α, (G) MIP1β and (H) RANTES in comparison to differentiated macrophages from Ldlr$^{-/-}$ mice. Data shown are comparison of M1 cells derived from Ldlr$^{-/-}$ EO6scFv$^{+/+}$ or Ldlr$^{-/-}$ mice. Similar data were found from M2 cells, e.g., less expression from M2 cells of Ldlr$^{-/-}$ EO6 scFv$^{+/+}$ compared to Ldlr$^{-/-}$, except the absolute levels of cytokine expression was less.

FIG. 11 the robust gene expression of the EO6-scFv mRNA in different adipose tissue derived from the Ldlr$^{-/-}$ EO6 scFv$^{+/+}$ mice. This is due to macrophage infiltration. Macrophages express the apoE promoter, and thus express the EO6-scFv transgene.

FIG. 13A-F indicates that there was less measurable atherosclerosis in Ldlr$^{-/-}$ EO6scFv$^{+/+}$ RAG1$^{-/-}$ mice vs. Ldlr$^{-/-}$ RAG1$^{-/-}$ mice. As RAG1 KO mice do not have B or T cells, all atherosclerosis events related to immunological cells are directly attributable to the action of macrophages. Notably, the absolute level of atherosclerosis of the Ldlr$^{-/-}$ RAG1$^{-/-}$ mice was reduced by half in comparison to Ldlr$^{-/-}$ mice. (A) Abdominal aortas isolated from Ldlr$^{-/-}$ RAG1$^{-/-}$ mice (left) and from Ldlr$^{-/-}$ EO6scFv$^{+/+}$ RAG1$^{-/-}$ mice (right). The abdominal aortas Ldlr$^{-/-}$ EO6scFv$^{+/+}$ RAG1$^{-/-}$ mice demonstratively had less atherosclerotic lesions than Ldlr$^{-/-}$ RAG1$^{-/-}$ mice. (B) The aortic sinus lesion size was significantly smaller for Ldlr$^{-/-}$ EO6scFv$^{+/+}$ RAG1$^{-/-}$ mice v. Ldlr$^{-/-}$ RAG1$^{-/-}$ mice. (C) Ldlr$^{-/-}$ RAG1$^{-/-}$ mice had a higher percentage of total body lesions vs. Ldlr$^{-/-}$ EO6scFv$^{+/+}$ RAG1$^{-/-}$ mice. (D) Ldlr$^{-/-}$ RAG1$^{-/-}$ mice had a higher percentage of abdominal lesions vs. Ldlr$^{-/-}$ EO6scFv$^{+/+}$ RAG1$^{-/-}$ mice. (E) The weight of aortas from Ldlr$^{-/-}$ RAG1$^{-/-}$ mice were significantly higher than the aortas from Ldlr$^{-/-}$ EO6scFv$^{+/+}$ RAG1$^{-/-}$ mice. (F) When controlled for body mass, the aorta per body mass from Ldlr$^{-/-}$ RAG1$^{-/-}$ mice was significantly higher than the aorta per body mass from Ldlr$^{-/-}$ EO6scFv$^{+/+}$ RAG1$^{-/-}$ mice. Because RAG1 KO mice lack both B and T cells, the major immunological cell type promoting atherosclerosis in these mice the macrophage. Thus, these data indicate that a major mechanism by which macrophages contribute to atherosclerosis in this TLR2 induced model is due to responses of OxPL.

FIG. 14 presents images of children with Kawasaki Disease, and further, coronary and abdominal artery aneurysms associated with the Kawasaki Disease.

FIG. 21 presents further cross-sections of aortic roots from Ldlr$^{-/-}$ TLR2$^{-/-}$ mice and from IK17-Tg$^{+/+}$ Ldlr$^{-/-}$ mice treated with LCWE. The arrows point to the coronary arteries in the cross section. The lack of arteritis in coronary arteries in the Ldlr$^{-/-}$ TLR2$^{-/-}$ mice indicates the importance of TLR2 activation in the mouse model of Kawasaki Disease.

DETAILED DESCRIPTION

Figure 1A:
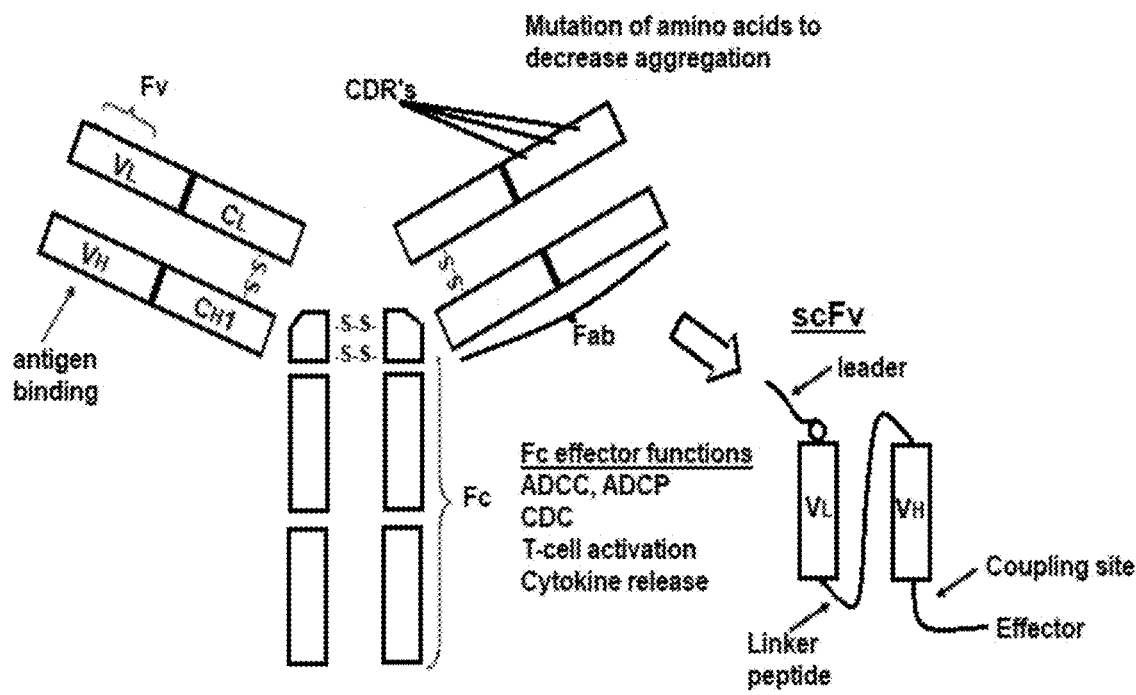
FIG. 1A-B provides (A) a diagram of the process that can be used to produce a single-chain variable fragment ("scFv"). As indicated, site directed mutagenesis can be employed to mutate the variable domain of the heavy chain ("$V_H$") of a double chain immunoglobulin antibody to increase the solubility of scFv (left). Linker, leader, and effector regions of the scFv are also indicated (right). (B) Provides a generalized map demonstrating the layout of the genetic components that encode the scFv EO6 antibody fragment (top); and a generalized vector map indicating the encoding sequence for the EO6-scFv antibody fragment in relation to other vector elements that was used to generate transgenic mice (bottom).

As used herein and in the appended claims, the singular forms "a," "an," and "the" include plural referents unless the context clearly dictates otherwise. Thus, for example, reference to a "single-chain variable fragment" or "scFv" includes a plurality of single-chain variable fragments and reference to "oxidized phospholipid" includes reference to one or more oxidized phospholipids and equivalents thereof known to those skilled in the art, and so forth.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

All publications mentioned herein are incorporated herein by reference in full for the purpose of describing and disclosing the methodologies, which are described in the publications, which might be used in connection with the description herein. Moreover, with respect to any term that is presented in one or more publications that is similar to, or identical with, a term that has been expressly defined in this disclosure, the definition of the term as expressly provided in this disclosure will control in all respects.

Also, the use of "and" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

The terms "antibody" and "immunoglobulin" are used interchangeably in the broadest sense and include monoclonal antibodies (e.g., full length or intact monoclonal antibodies), polyclonal antibodies, multivalent antibodies, multispecific antibodies (e.g., bispecific antibodies so long as they exhibit the desired biological activity) and may also include certain antibody fragments. An antibody can be human, humanized and/or affinity matured.

Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., IgG$_1$, IgG$_2$, IgG$_3$, IgG$_4$, IgA$_1$, and IgA$_2$. The heavy-chain constant domains that correspond to the different classes of immunoglobulins are called α, δ, ε, γ, and μ, respectively. The subunit structures and three-dimensional configurations of different classes of immunoglobulins are well known.

"Antibody fragments" comprise only a portion of an intact antibody, wherein the portion typically retains at least one, more commonly most or all, of the functions normally associated with that portion when present in an intact antibody. Examples of antibody fragments include Fab, Fab', F(ab')$_2$, and Fv fragments; diabodies; linear antibodies; single-chain antibody molecules; and multispecific antibodies formed from antibody fragments. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half-life modulation, ADCC function and complement binding. In one embodiment, an antibody fragment is a monovalent antibody that has an in vivo half-life substantially similar to an intact antibody. For example, such an antibody fragment may comprise on antigen binding arm linked to an Fc sequence capable of conferring in vivo stability to the fragment. It should be recognized however, a long half-life of the antibody is not necessary for certain indication (e.g., acute ishemic/reperfusion treatments).

An "antigen" is a predetermined antigen to which an antibody can selectively bind. The target antigen may be polypeptide, carbohydrate, nucleic acid, lipid, hapten or other naturally occurring or synthetic compound. In one embodiment, of the disclosure an antigen is an OxPL.

The term "anti-OxPL antibody" or "an antibody that binds to OxPL" refers to an antibody that is capable of binding OxPL with sufficient affinity such that the antibody is useful as a diagnostic and/or therapeutic agent in targeting OxPL. In some embodiments of the disclosure an anti-OxPL antibody has the same or a similar binding specificity and K$_d$ as the EO6 antibody or the QX5 antibody. In yet another embodiment, the anti-OxPL antibody binds to the PC headgroup of OxPLs.

A "blocking" antibody or an "antagonist" antibody is one which inhibits or reduces biological activity of the antigen it binds. Certain blocking antibodies or antagonist antibodies substantially or completely inhibit the biological activity of the antigen.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (K$_d$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides, or embedding in a semi-solid or solid matrix for sectioning purposes. The term "biological sample" encompasses a clinical sample, and also includes cells in culture, cell supernatants, cell lysates, serum, plasma, biological fluid, and tissue samples. The source of the biological sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. In some embodiments, the biological sample is obtained from a primary or metastatic tumor. The biological sample may contain compounds which are not naturally intermixed with the tissue in nature such as preservatives, anticoagulants, buffers, fixatives, nutrients, antibiotics, or the like.

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993). Triabodies and tetrabodies are also described in Hudson et al., Nat. Med. 9:129-134 (2003).

A "disorder" or "disease" is any condition that would benefit from treatment with a substance/molecule or method of the disclosure. This includes TLR2 mediated disease or disorders, such as Kawasaki disease.

An "effective amount" refers to an amount effective, at dosages and for periods of time necessary, to achieve the desired therapeutic or prophylactic result.

The term "Fc region" as used herein refers to the C-terminal region of an immunoglobulin heavy chain, including native sequence Fc regions and variant Fc regions.

A "functional Fc region" possesses an effector function of a native sequence Fc region. Such effector functions generally require the Fc region to be combined with a binding to domain (e.g., an antibody variable domain) and can be assessed using various assays as disclosed, for example, in definitions herein.

A "native sequence Fc region" comprises an amino acid sequence that is identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

"Fc receptor" or "FcR" describes a receptor that binds to the Fc region of an antibody. In some embodiments, an FcR is a native human FcR. In other embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof.

Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see, e.g., Daeron, Annu. Rev. Immunol. 15:203-234 (1997)). FcRs are reviewed, for example, in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein.

Fc receptor also include the neonatal receptor, FcRn, which is responsible for the transfer of maternal IgGs to the fetus (Guyer et al., J. Immunol. 117:587 (1976) and Kim et al., J. Immunol. 24:249 (1994)) and regulation of homeostasis of immunoglobulins. Methods of measuring binding to FcRn are known (see, e.g., Ghetie and Ward., Immunol. Today 18(12):592-598 (1997); Ghetie et al., Nature Biotechnology, 15(7):637-640 (1997); Hinton et al., J. Biol. Chem. 279(8):6213-6216 (2004); WO 2004/92219 (Hinton et al.).

Binding to human FcRn in vivo and serum half-life of human FcRn high affinity binding polypeptides can be assayed, e.g., in transgenic mice or transfected human cell lines expressing human FcRn, or in primates to which the polypeptides with a variant Fc region are administered. WO 2000/42072 (Presta) describes antibody variants with improved or diminished binding to FcRs. See also, e.g., Shields et al., J. Biol. Chem. 9(2):6591-6604 (2001).

"Fv" is the minimum antibody fragment which contains a complete antigen-recognition and -binding site. In a two-chain Fv species, this region consists of a dimer of one heavy- and one light-chain variable domain in tight, non-covalent association. In a single-chain Fv species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains have a free thiol group. F(ab')$_2$ antibody fragments originally were produced as pairs of Fab' fragments which have hinge cysteines between them. Other chemical couplings of antibody fragments are also known.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Framework" or "FR" residues are those variable domain residues other than the hypervariable region residues as herein defined.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a HVR of the recipient are replaced by residues from a HVR of a non-human species (donor antibody) such as mouse, rat, rabbit, or nonhuman primate having the desired specificity, affinity, and/or capacity. In some instances, framework residues of the human immunoglobulin are replaced by corresponding non-human residues. Furthermore, humanized antibodies may comprise residues that are not found in the recipient antibody or in the donor antibody. These modifications may be made to further refine antibody performance.

In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. For further details, see, e.g., Jones et al., Nature 321:522-525 (1986); Riechmann et al., *Nature* 332: 323-329 (1988); and Presta, *Curr. Op. Struct. Biol.* 2:593-596 (1992). See also, e.g., Vaswani and Hamilton, Ann. *Allergy, Asthma & Immunol.* 1:105-115 (1998); Harris, *Biochem. Soc. Transactions* 23:1035-1038 (1995); Hurle and Gross, *Curr. Op. Biotech,* 5:428-433 (1994); and U.S. Pat. Nos. 6,982,321 and 7,087,409.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.,* 227: 381 (1991); Marks et al., *J. Mol. Biol.,* 222:581 (1991). Also available for the preparation of human monoclonal antibodies are methods described in Cole et al., Monoclonal Antibodies and Cancer Therapy, Alan R. Liss, p. 77 (1985); Boerner et al., J. Immunol., 147(1):86-95 (1991). See also van Dijk and van de Winkel, *Curr. Opin. Pharmacol.,* 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584). See also, for example, Li et al., Proc. Natl. Acad. Sci. USA, 103:3557-3562 (2006) regarding human antibodies generated via a human B-cell hybridoma technology. It should be important to note that a "human antibody" does not include naturally occurring antibodies produced by a human, but rather refer to antibodies that do not contain any epitope or antigenic fragment a human subject would not recognize as "foreign".

"Human effector cells" are leukocytes which express one or more FcRs and perform effector functions. In certain embodiments, the cells express at least FcγRIII and perform ADCC effector function(s). Examples of human leukocytes which mediate ADCC include peripheral blood mononuclear cells (PBMC), natural killer (NK) cells, monocytes, cytotoxic T cells, and neutrophils. The effector cells may be isolated from a native source, e.g., from blood.

The term "hypervariable region," "HVR," or "HV," when used herein refers to the regions of an antibody variable domain which are hypervariable in sequence and/or form structurally defined loops. Generally, antibodies comprise six HVRs; three in the $V_H$ domain (H1, H2, H3), and three in the $V_L$ domain (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu, in Methods in Molecular Biology 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., *Nature* 363:446-448 (1993); Sheriff et al., *Nature Struct. Biol.* 3:733-736 (1996).

An "individual," "subject," or "patient" is a vertebrate. In certain embodiments, the vertebrate is a mammal. Mammals include, but are not limited to, farm animals (such as cows), sport animals, pets (such as cats, dogs, and horses), primates, mice and rats. In certain embodiments, a mammal is a human.

An "isolated" antibody or antibody fragment is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In some embodiments, the antibody will be purified (1) to greater than 95% by weight of antibody as determined by the Lowry method, and typically more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or silver stain. An isolated antibody includes the antibody in situ within recombinant cells since at least one component of the antibody's natural environment will not be present. Ordinarily, however, an isolated antibody will be prepared by at least one purification step.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The word "label" when used herein refers to a compound or composition which is conjugated or fused directly or indirectly to a reagent such as a nucleic acid probe or an antibody and facilitates detection of the reagent to which it is conjugated or fused. The label may itself be detectable (e.g., radioisotope labels or fluorescent labels) or, in the case of an enzymatic label, may catalyze chemical alteration of a substrate compound or composition which is detectable.

The "light chains" of antibodies (immunoglobulins) from any vertebrate species can be assigned to one of two clearly distinct types, called kappa (κ) and lambda (λ), based on the amino acid sequences of their constant domains.

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier term "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody for purposes of this disclosure. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier term "monoclonal" indicates the character of the antibody as being obtained from a substantially homogeneous population of antibodies, and is not to be construed as requiring production of the antibody by any particular method. For example, the monoclonal antibodies to be used in accordance with the disclosure may be made by a variety of techniques, including, for example, the hybridoma method (e.g., Kohler and Milstein, *Nature*, 256: 495-97 (1975); Hongo et al., Hybridoma, 14 (3): 253-260 (1995), Harlow et al., Antibodies: A Laboratory Manual, (Cold Spring Harbor Laboratory Press, 2nd ed. 1988); Hammerling et al., in: Monoclonal Antibodies and T-Cell Hybridomas 563-681 (Elsevier, N.Y., 1981)), recombinant DNA methods (see, e.g., U.S. Pat. No. 4,816,567), phage-display technologies (see, e.g., Clackson et al., *Nature*, 352: 624-628 (1991); Marks et al., *J. Mol. Biol.* 222: 581-597 (1992); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., Nature 362: 255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10: 779-783 (1992); Lonberg et al., *Nature* 368: 856-859 (1994); Morrison, Nature 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; and Morrison et al., *Proc. Natl. Acad. Sci.* USA 81:6851-6855 (1984)). Chimeric antibodies include antibodies wherein the antigen-binding region of the antibody is derived from an antibody produced by, e.g., immunizing macaque monkeys with the antigen of interest.

A "polynucleotide," or "nucleic acid," as used herein, refer to polymers of nucleotides of any length, and include DNA and RNA. The nucleotides can be deoxyribonucleotides, ribonucleotides, modified nucleotides or bases, and/or their analogs that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

Figure 1B:
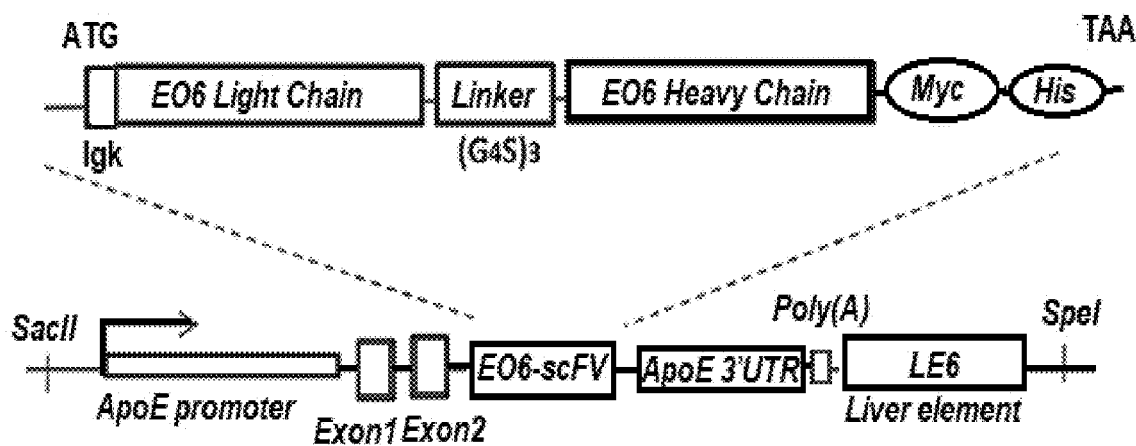
Figure 4C:
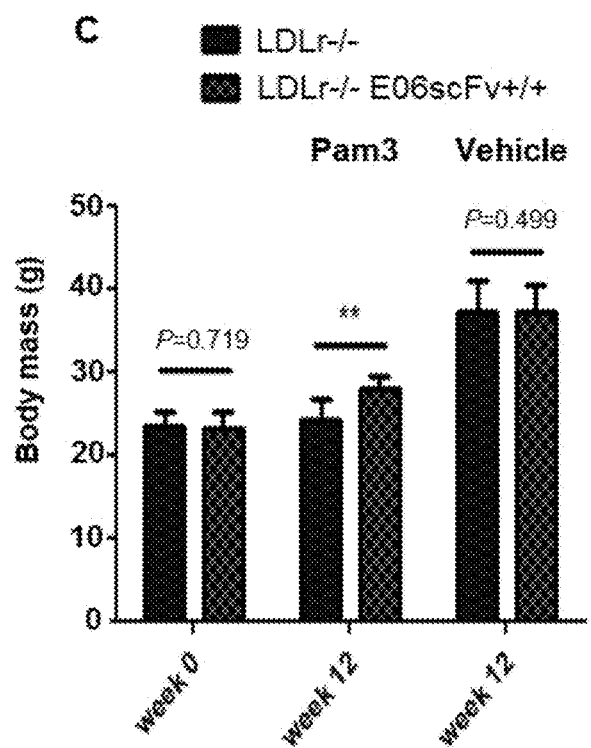
Figure 5A:
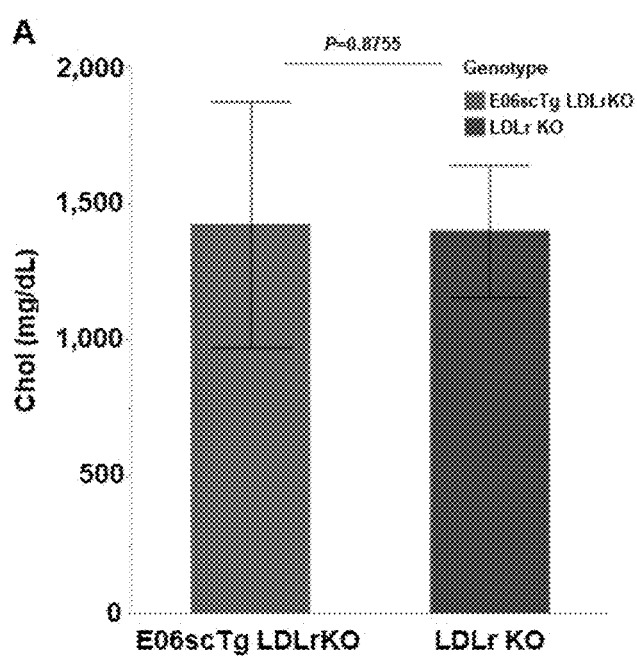
FIG. 5A-B demonstrates that there were no significant differences in (A) cholesterol or (B) triglycerides in blood plasma of EO6scTg Ldlr$^{-/-}$ (LDLrKO (knock-out)) mice vs. Ldlr$^{-/-}$ mice.
Figure 5B:
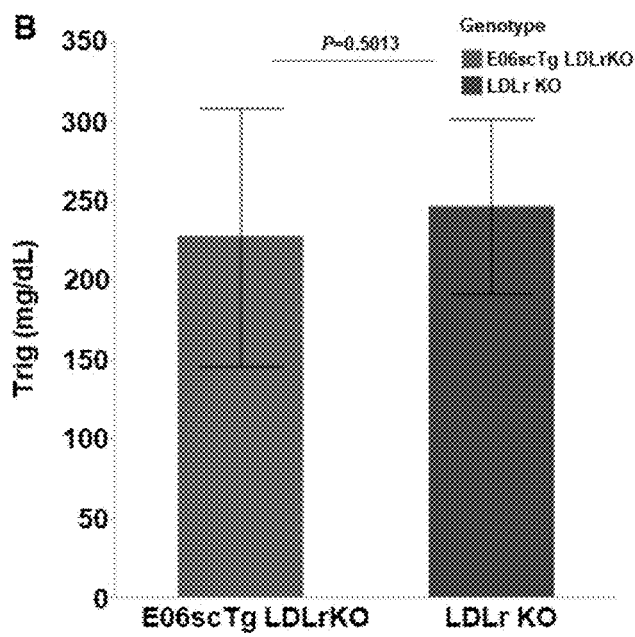
Figure 6A:
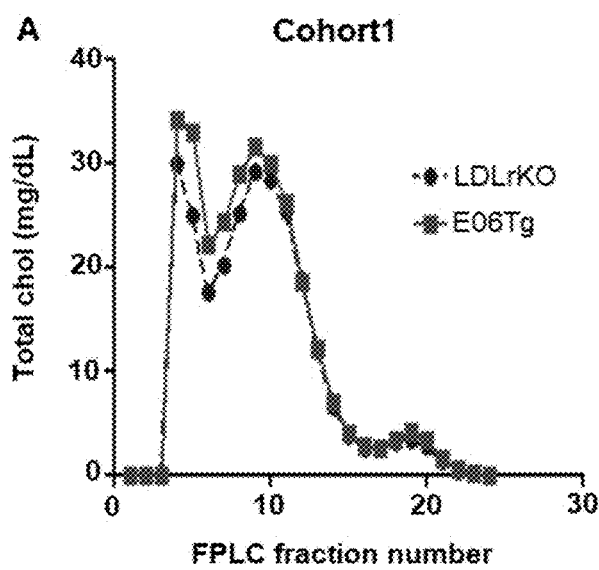
Figure 12:
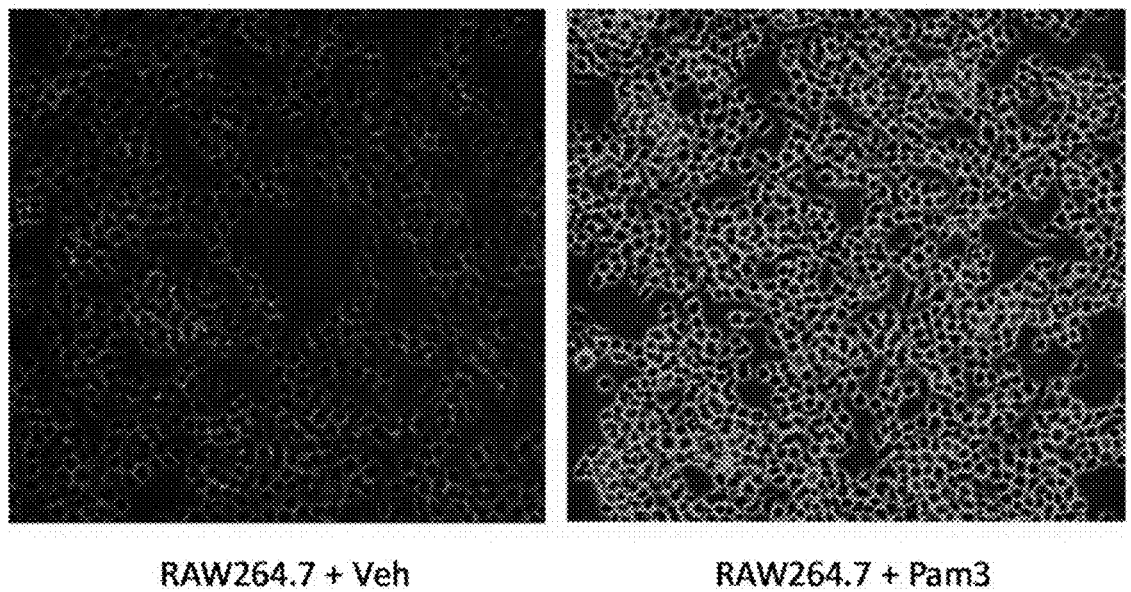
FIG. 12 provides fluorescence microscope images indicating that treatment of macrophages (RAW264.7) with PAM3 induced the production of OxPL. Because macrophages from Ldlr$^{-/-}$ EO6scFv$^{+/+}$ mice were less responsive to TLR2 stimulation, and because macrophages express and secrete EO6-scFv into the culture, it was postulated that TLR2 stimulated macrophages generated OxPL, and that this in turn activated inflammatory gene expression in an autocrine manner. To test this hypothesis macrophages were stimulated with PAM3: Left panel, treatment with vehicle; right panel, treatment with the TLR2 agonist, PAM3. RAW264.7 cultures were incubated with Pam3 (1 µg/mL) or control vehicle for 18 h, and surface stained for OxPL with EO6 IgM antibody and Goat anti-ms IgM-FITC conjugate. This demonstrates that TLR2 stimulated macrophages generate OxPL.
Figure 13A:
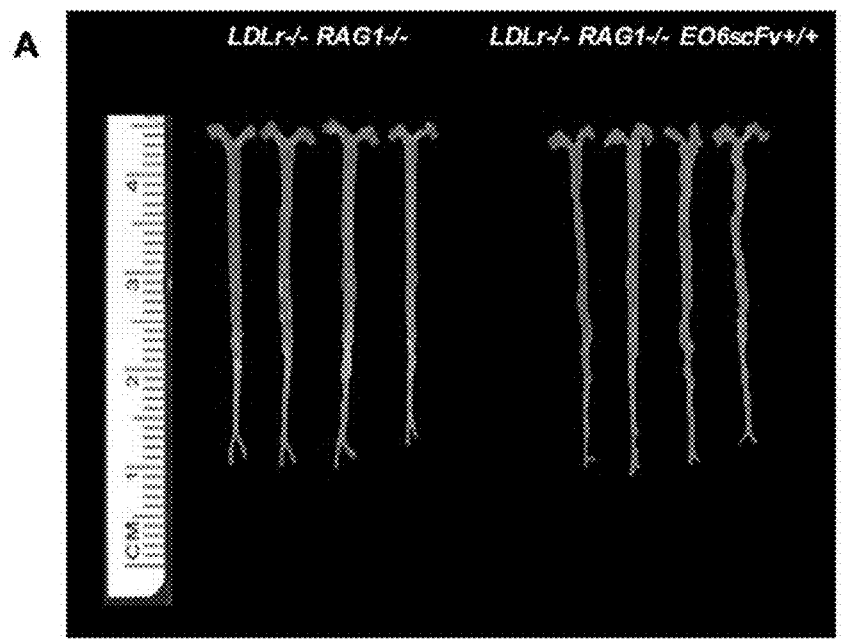
Figure 15:
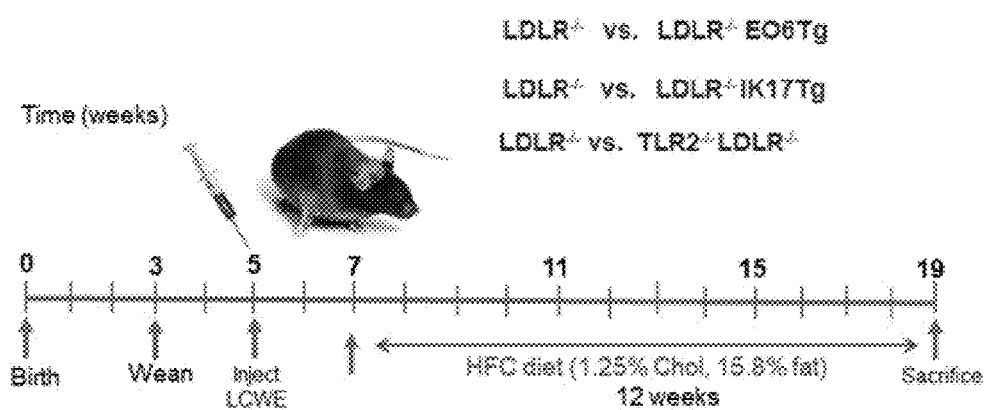
FIG. 15 presents a mouse model to study the impact of LCWE, and HFC diet on atherosclerosis in Ldlr$^{-/-}$ mice, Ldlr$^{-/-}$ EO6Tg mice, Ldlr$^{-/-}$ IK17Tg mice, TLR2$^{-/-}$ Ldlr$^{-/-}$ mice.
Figure 16:
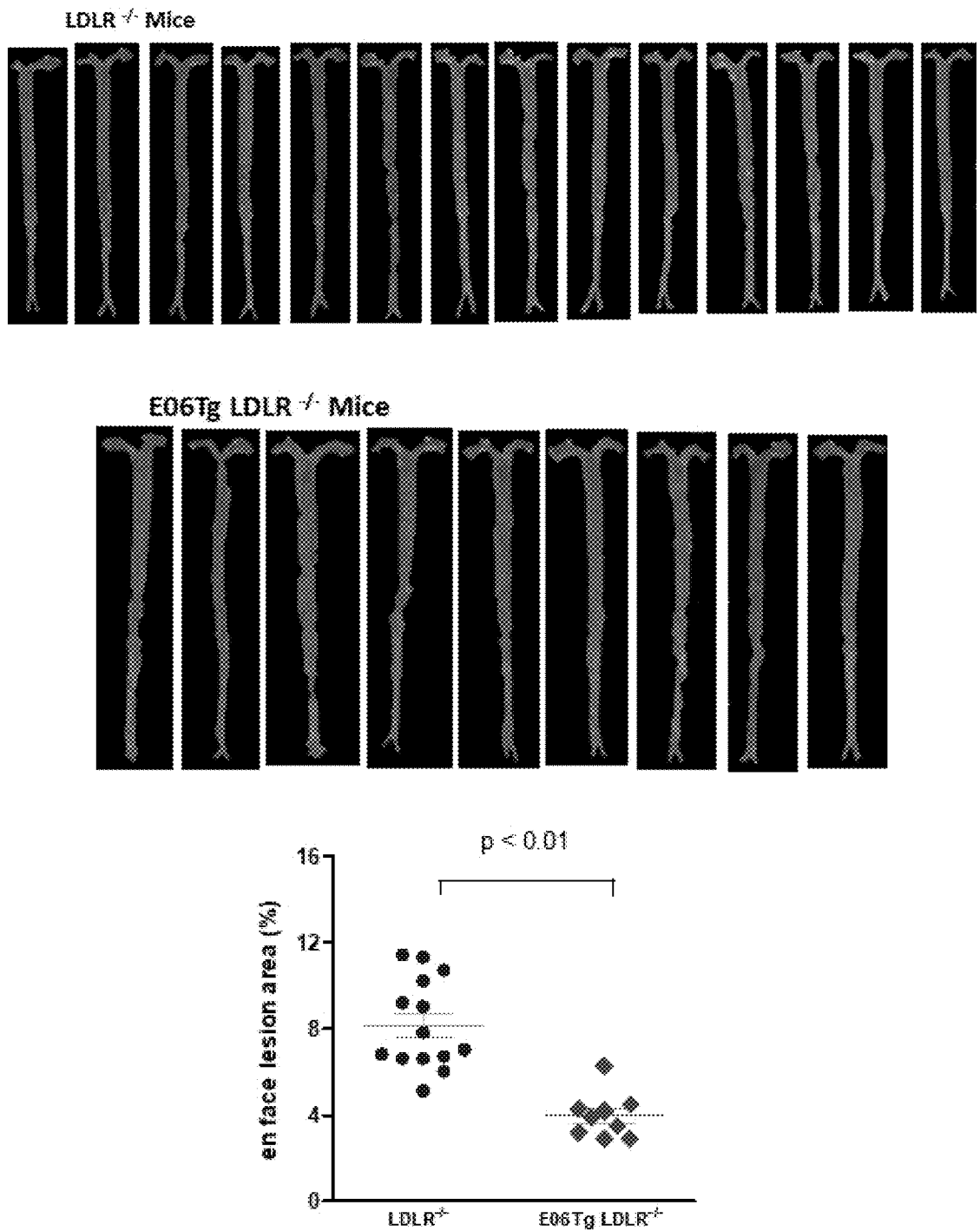
FIG. 16 presents en face analysis of aortic lesions in mice fed HFC diet for 12-wk and TLR2 activated by LCWE. EO6scFv-Tg reduced en face aortic lesions significantly.
Figure 17:
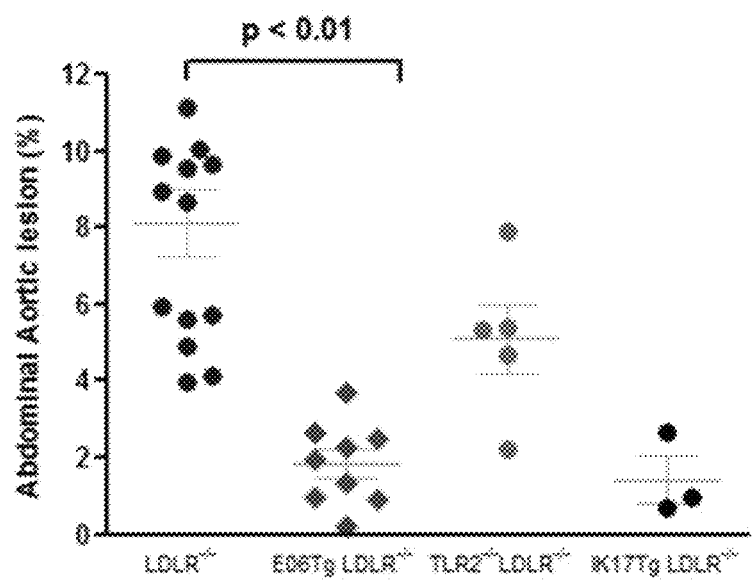
FIG. 17 provides analysis of the abdominal aortic lesion area in various Ldlr$^{-/-}$ mice injected with LCWE and fed with HFC diet for 12-wks. Data are expressed as the percentage of atherosclerosis measured in the abdominal aorta by Sudan IV staining. EO6Tg and IK17Tg were found to exert a statistically significant protective effect. TLR2 was also found to statistically decrease in comparison to the Ldlr$^{-/-}$ mice as well.
Figure 18:
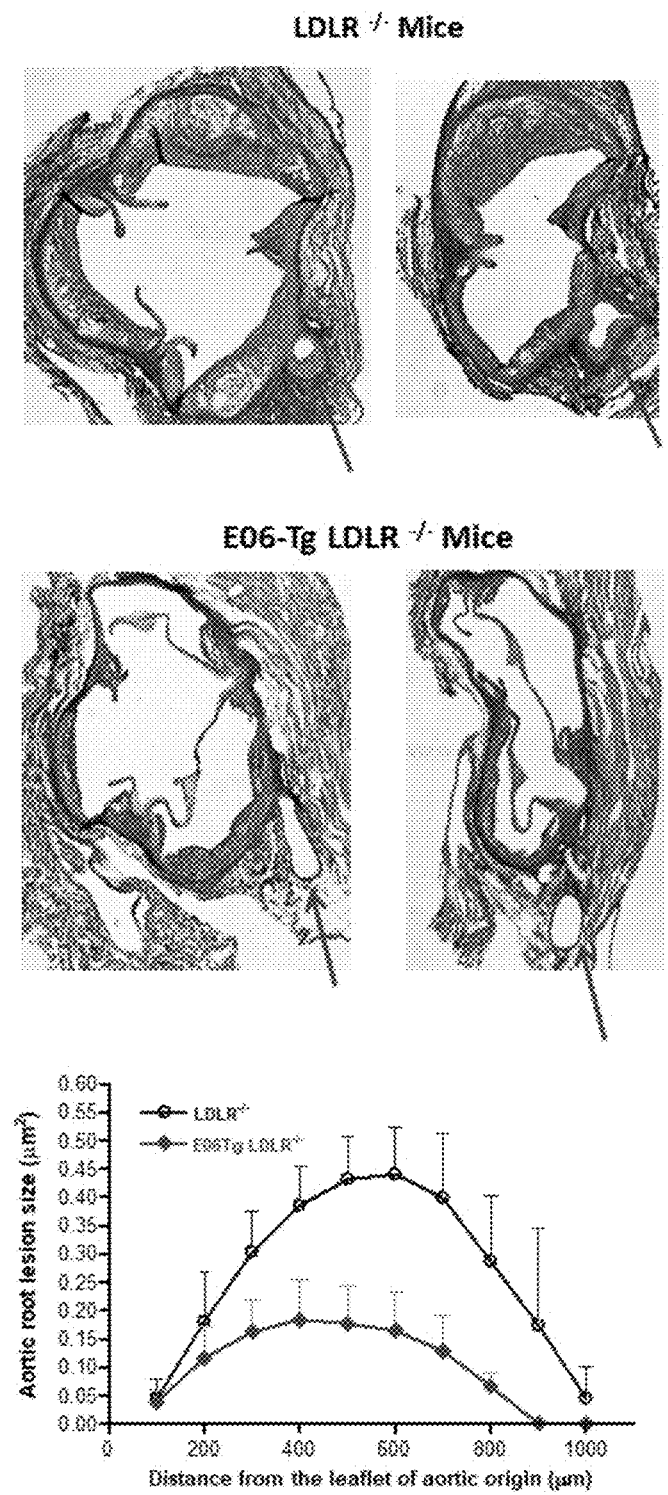
FIG. 18 presents cross-sections of aortic roots from Ldlr$^{-/-}$ mice and from EO6-Tg Ldlr$^{-/-}$ mice treated with LCWE. EO6scFv-Tg reduced the aortic root lesions, necrotic core size and most importantly in the context of Kawasaki disease manifestations, coronary arteritis. The arrows point to the coronary arteries in the cross section. Extensive arteritis (large cell mass) was present in the Ldlr$^{-/-}$ mice but missing in the EO6-Tg Ldlr$^{-/-}$ mice.
Figure 19:
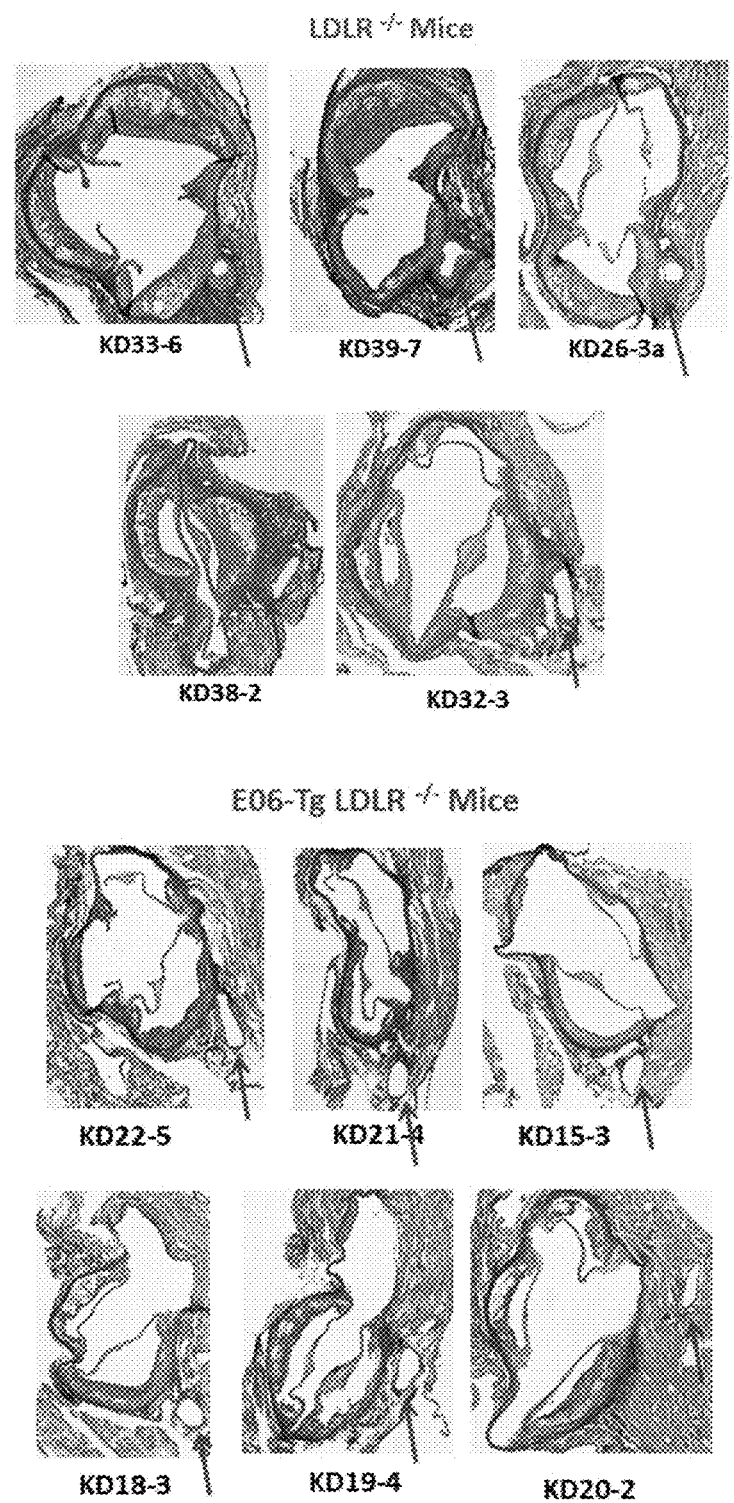
FIG. 19 presents further cross-sections of aortic roots from Ldlr$^{-/-}$ mice and from EO6-Tg Ldlr$^{-/-}$ mice treated with LCWE. The arrows point to the coronary arteries in the cross section. Extensive arteritis (large cell mass) was present in the Ldlr$^{-/-}$ mice but missing in the EO6-Tg Ldlr$^{-/-}$ mice.
Figure 20:
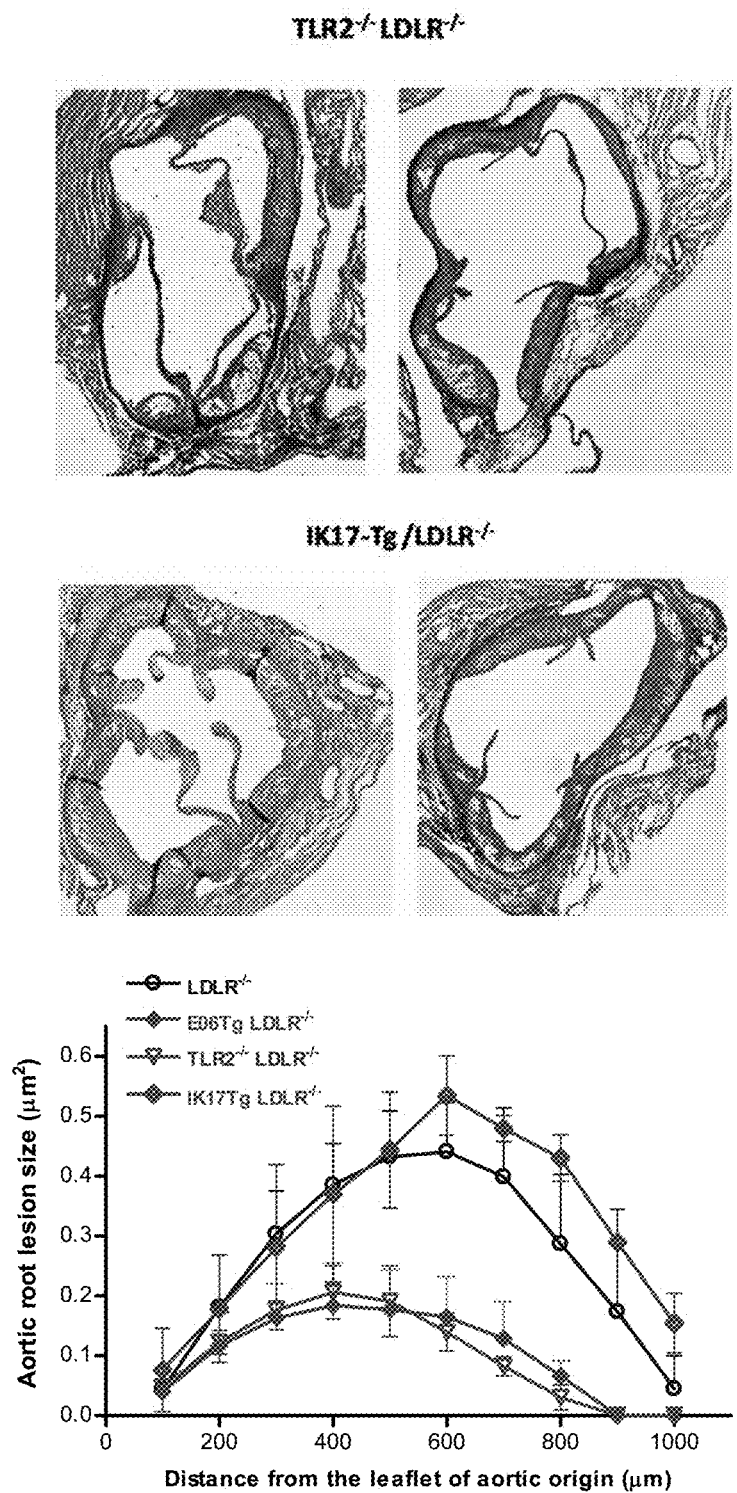
FIG. 20 presents cross-sections of aortic roots from Ldlr$^{-/-}$ TLR2$^{-/-}$ mice and from IK17-Tg$^{+/+}$ Ldlr$^{-/-}$ mice treated with LCWE. The arrows point to the coronary arteries in the cross section. Both EO6scFv and IK17scFv decreased coronary arteritis. EO6 (Anti-OxPL) but not IK17 (anti-MDA) reduced the aortic root lesions.
Figure 22:
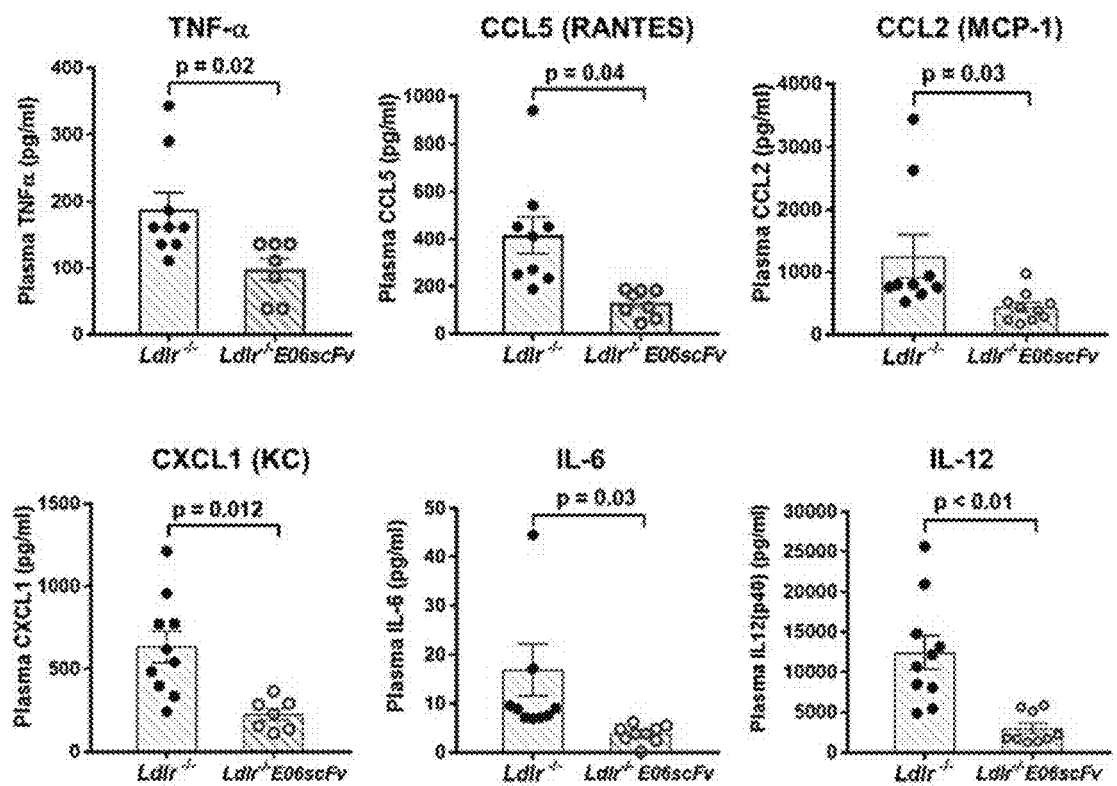
FIG. 22 depicts plasma inflammatory cytokine levels of Ldlr$^{-/-}$ control mice and EO6-Tg Ldlr$^{-/-}$ mice treated with LCWE and fed HFC diets for 12 wks. The plasma cytokines were measured by multiplex cytokine assays simultaneously using Bio-Plex Pro mouse cytokine assay kit (Bio-Rad Laboratories, USA). Significant reduction ($p<0.04$) in serum TNFa, RANTES, MCP-1, CXCL1, IL-6, and IL-12 protein levels was observed in EO6scFv-Tg Ldlr$^{-/-}$ mice compared to control mice.

"Single-chain Fv" or "scFv" antibody fragments comprise the V$_H$ and V$_L$ domains of antibody, wherein these domains are present in a single polypeptide chain. Generally, the scFv polypeptide further comprises a polypeptide linker between the V$_H$ and V$_L$ domains which enables the scFv to form the desired structure for antigen binding. FIG. 1 shows an antibody and scFv structure. For a review of scFv see Pluckthun, in The Pharmacology of Monoclonal Antibodies, vol. 113, Rosenburg and Moore eds., Springer-Verlag, New York, pp. 269-315 (1994).

The term "substantially similar" or "substantially the same," as used herein, denotes a sufficiently high degree of similarity between two numeric values (for example, one associated with an antibody of the disclosure and the other associated with a reference/comparator antibody), such that one of skill in the art would consider the difference between the two values to be of little or no biological and/or statistical significance within the context of the biological characteristic measured by the values (e.g., $K_d$ values). The difference between said two values is, for example, less than about 50%, less than about 40%, less than about 30%, less than about 20%, and/or less than about 10% as a function of the reference/comparator value.

The phrase "substantially reduced," or "substantially different," as used herein, denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., $K_d$ values). The difference between said two values is, for example, greater than about 10%, greater than about 20%, greater than about 30%, greater than about 40%, and/or greater than about 50% as a function of the value for the reference/comparator molecule.

"TLR2 related disease and disorders" includes, but are not limited to autoimmune diseases including rheumatoid arthritis, systemic lupus erythematosus, systemic sclerosis, Sjögren's syndrome, psoriasis, multiple sclerosis, and autoimmune diabetes. TLR-related conditions (e.g., directly and/or indirectly associated with TLRs such as TLR2, etc.) can include any one or more of: diabetes, obesity, sepsis, inflammatory disease (e.g., Crohn's disease), immune disorders, metabolic disease (e.g., conditions associated with metabolic syndrome), endocrine disease, atherosclerosis, asthma, cardiovascular disease, immune-related conditions, and/or any other suitable conditions. For example, the TLR2-mediated disease or disorder can be selected from the group consisting of Kawasaki disease, type 2 diabetes, rheumatoid arthritis, dermatologic disease, multiple sclerosis, systemic lupus erythematosus, ulcerative colitis, Graves' Disease, Sjögren's syndrome, autoimmune thyroid diseases, vasculitis and any combination thereof.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, decreasing the rate of disease progression, amelioration or palliation of the disease state, and remission or improved prognosis. In some embodiments, an antibody (humanized or non-humanized), antibody fragment, or polypeptide of the disclosure or a humanized antibody of the disclosure are used to delay development of a disease or disorder.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions or hypervariable regions (CDRs or HVRs, used interchangeably herein) both in the light-chain and the heavy-chain variable domains. The more highly conserved portions of variable domains are called the framework (FR). The variable domains of native heavy and light chains each comprise four FR regions, largely adopting a (3-sheet configuration, connected by three HVRs, which form loops connecting, and in some cases forming part of, the (3-sheet structure. The HVRs in each chain are held together in close proximity by the FR regions and, with the HVRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell and replicate along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids.

A "variant Fc region" comprises an amino acid sequence which differs from that of a native sequence Fc region by virtue of at least one amino acid modification, typically one or more amino acid substitution(s). Typically, the variant Fc region has at least one amino acid substitution compared to a native sequence Fc region or to the Fc region of a parent polypeptide, e.g. from about one to about ten amino acid substitutions, and typically from about one to about five amino acid substitutions in a native sequence Fc region or in the Fc region of the parent polypeptide. The variant Fc region of a disclosure possesses at least about 80% homology with a native sequence Fc region and/or with an Fc region of a parent polypeptide, at least about 90% homology therewith, and typically at least about 95% homology therewith.

"Oxidized phospholipids" (OxPL) refer to phospholipids with a phosphocholine (PC) headgroup. OxPL are highly pro-inflammatory and proatherogenic. Phosphorylcholine, a polar head group on certain phospholipids, has been extensively implicated in cardiovascular disease. Reactive oxygen species generated during coronary inflammation causes the oxidation of low density lipoprotein (LDL) to generate oxidized LDL (oxLDL). In fact, cardiovascular diseases (CVD) such as atherosclerosis, unstable angina, or acute coronary syndrome have been shown to be associated with elevated plasma levels of oxLDL. LDL is a circulating lipoprotein particle that contains lipids with a PC polar head group and proteins, an apoB100 protein.

During oxidation of LDL PC containing neo-epitopes that are not present on unmodified LDL are generated. Newly exposed PC on oxLDL is recognized by scavenger receptors on macrophages, such as CD36, and the resulting macrophage-engulfed oxLDL proceeds towards the formation of proinflammatory foam cells in the vessel wall. Oxidized LDL is also recognized by receptors on endothelial cell surfaces and has been reported to stimulate a range of responses including endothelial dysfunction, apoptosis, and the unfolded protein response. PC neo-epitopes are also exposed on LDL following modification with phospholipase A2 or amine reactive disease metabolites, such as aldehydes generated from the oxidation of glycated proteins. These alternately modified LDL particles are also pro-inflammatory factors in CVD. Antibodies towards phosphorylcholine (PC) have been shown to bind oxidized, or otherwise modified, LDL and block the pro-inflammatory activity of oxLDL in in vivo models or in vitro studies.

Glycerophospholipids represent a common class of lipids important for integrity of cellular membranes. Oxidation of esterified unsaturated fatty acids dramatically changes biological activities of phospholipids. Apart from impairment of their structural function, oxidation makes oxidized phospholipids (OxPLs) markers of "modified-self" type that are recognized by soluble and cell-associated receptors of innate immunity, including scavenger receptors, natural (germ line-encoded) antibodies, and C-reactive protein, thus directing removal of senescent and apoptotic cells or oxidized lipoproteins. In addition, OxPLs acquire novel biological activities not characteristic of their unoxidized precursors, including the ability to regulate innate and adaptive immune responses. Effects of OxPLs described in vitro and in vivo suggest their potential relevance in different pathologies, including atherosclerosis, acute inflammation, lung injury, and many other conditions.

Glycerophospholipids comprise an abundant class of lipids consisting of a glycerol backbone, phosphate-containing polar head group and two fatty acid residues. PL-bound polyunsaturated fatty acids (PUFAs) represent the major target for nonenzymatic or enzymatic oxidation that is not linked to the generation of metabolic energy. Oxidative fragmentation of a PL molecule generates several biologically active products, including small chemically reactive fragments of PUFAs, such as unesterified oxidized fatty acids (e.g., hydroperoxides and isoprostanes) and lysophospholipids. These products demonstrate multiple biological activities. Available evidence suggests that nonenzymatic oxidation of PL-PUFAs proceeds according to the same basic mechanisms as oxidation of free (unesterified) PUFAs. This assumption is supported by identification of similar classes of molecular species generated by oxidation of free and PL-bound PUFAs that are described herein. In contrast to the nonenzymatic oxidation, oxidation of PL-PUFAs by enzymes significantly differs from oxidation of unesterified PUFAs. While free PUFAs can be oxidized by multiple enzymes belonging to different protein families and introducing various oxidized groups, only one group of lipoxygenases (12/15 lipoxygenases) accepts PL-PUFAs as substrates producing PL-hydroperoxides. Further oxidation and rearrangements continue without participation of enzymes, and therefore oxidation initiated by enzymatic and nonenzymatic mechanisms produces many similar advanced PL oxidation products.

Toll-like receptor 2 also known as TLR2 is a protein that in humans is encoded by the TLR2 gene. TLR2 has also been designated as CD282 (cluster of differentiation 282). TLR2 plays a role in the immune system. TLR2 is a membrane protein receptor, which is expressed on the surface of certain cells and recognizes foreign substances and passes on appropriate signals to the cells of the immune system. TLR2 plays a fundamental role in pathogen recognition and activation of innate immunity. Toll like receptors (TLRs) are highly conserved from Drosophila to humans and share structural and functional similarities. They recognize pathogen-associated molecular patterns (PAMPs) that are expressed on infectious agents, and mediate the production of cytokines necessary for the development of effective immunity. The various TLRs exhibit different patterns of expression. This gene is expressed most abundantly in peripheral blood leukocytes, and mediates host response to Gram-positive bacteria and yeast via stimulation of NF-κB. TLR2 detects a large range of microbial components, such as gram-positive-derived lipoteichoic acid, bacterial lipoproteins, and zymosan. Of the 11 characterized TLRs, TLR2 is unique by virtue of its ability to heterodimerize with TLR1 or TLR6, resulting in a relatively broad ligand specificity.

CD36 by being a coreceptor for TLR2, has suggested that there is proinflammatory pathway existing between endogenously derived lipids and activation of innate immunity. Studies have further found enhanced endothelial TLR2 expression and activation occurring at areas of disturbed blood flow, such as the areas of lesion predilection within the aortic tree and heart. Thus, TLR2 expression may promote atherosclerosis in cells that are not of BM origin, such as endothelial cells, and thus may contribute to the proinflammatory phenotype of activated endothelial cells.

In atherosclerosis-susceptible low-density lipoprotein receptor-deficient (Ldlr$^{-/-}$) mice, complete deficiency of TLR2 led to a reduction in atherosclerosis. Loss of TLR2 expression from BM-derived cells had no effect on disease progression, however. The data suggests that an unknown endogenous TLR2 agonist influenced lesion progression by activating TLR2 in cells that were not of BM cell origin. As shown herein, intraperitoneal administration of a synthetic TLR2/TLR1 agonist, Pam3CSK4, disease burden was dramatically increased in Ldlr$^{-/-}$ mice. A complete deficiency of TLR2 in Ldlr$^{-/-}$ mice, as well as a deficiency of TLR2 only in BM-derived cells in Ldlr$^{-/-}$ mice, attenuated Pam3CSK4-mediated atherosclerosis, suggesting a role for BM-derived cell expression of TLR2 in transducing the effects of an exogenous TLR2 agonist.

OxPL can activate cell signaling via TLR2 mediated pathways, resulting in proinflammatory cell signaling. In addition, OxPL mediated activation of TLR2 can lead to apoptosis and cell death when done in association with signaling pathways that promote ER stress. OxPL induces IL-8 signaling from endothelial cells and induces IL-1β and TNFα signaling in macrophages via a TLR2-dependent signaling pathway. As further demonstrated herein, activation of macrophages via the synthetic TLR2 agonist, PAM3CSK4, directly stimulates macrophages to generate OxPL. It has also been reported that activation of TLR4 via agonists, such as LPS, will also lead macrophages to generate OxPLs (Popat et al., JCI, 2017). In aggregate, the data presented herein demonstrate that OxPL can both directly activate macrophages via TLR2 (or TLR4) to induce proinflammatory signaling and/or apoptosis, and that conversely, activation of macrophages via either TLR2 or TLR4 signaling will in turn cause macrophages to make OxPL. In the latter situation, when macrophages are stimulated by TLR2/4 agonists, the locally generated OxPL has the potentially to amplify and enhance the inflammatory pathway by auto-paracrine effects, Thus, the studies presented herein suggest that OxPL can both directly stimulate TLR2 pathways, as well as act in a paracrine fashion to amplify proinflammatory TLR2/4 agonist signaling. These insights explain why neutralizing OxPL with an antibody to OxPL in vivo, in a variety of inflammatory settings, confers such profound anti-inflammatory effects that are manifested in reduced disease development.

The data suggest that the antibodies, or fragments thereof, that bind OxPL, including EO6, or others designed to bind the phosphocholine (PC) headgroups of PC-containing oxidized phospholipids (OxPL), could be useful in ameliorating the deleterious effects of TLR2 agonism present in wide variety of diseases. These, include atherosclerosis, autoimmune disorders and specifically in Kawasaki Disease, a disease of children of unknown origin in which TLR2 mediated agonism is believe to promote coronary arteritis that leads to coronary aneurysms, severe coronary calcification, disordered coronary blood flow, acute thrombosis and major morbidity and death. The disease can also affect young adults when asymptomatic coronary aneurysms transition to acute thrombosis causing acute myocardial infarction. Kawasaki disease can also be associated with myocarditis, heart failure and need for heart transplantation.

Innate natural antibodies (NAbs) provide the first line of host defense against common oxidation-specific epitopes (OSE) on endogenous neo-epitopes (OxLDL and apoptotic cells) and exogenous epitopes of pathogens, and maintain host homeostasis. OSEs are ubiquitous, formed in many inflammatory tissues, including atherosclerotic lesions, and are a major target of IgM NAbs. The prototypic IgM NAb EO6, binds to the phosphocholine (PC) headgroup in oxidized phospholipids (OxPL), and blocks uptake of OxLDL by macrophages. A murine IgM natural antibody to OxPL that binds to the phosphorylcholine ("PC") headgroup of OxPL but not to native, non-oxidized phospholipids ("PL") has been cloned and characterized. However, antibodies like IgM Nab EO6 have limited solubility and cannot be readily synthesized.

The parent EO6 antibody is a murine IgM antibody that was cloned and characterized and which is the subject of U.S. Pat. No. 6,225,070, which is incorporated herein by reference. U.S. Patent Publication No. 20150376268A1 describes a fully functional single chain antibody and humanized antibodies that bind to OxPL. It describes the numerous unique molecular changes to the DNA sequence of the parent antibody framework regions, heavy and light chains, and a linker sequences that was determined by repeated rounds of experimentation, which resulted in the development of a fully functional EO6-scFv. When this sequence was inserted into the appropriate vector, the resultant scFc is expressed in a soluble form, and possesses all the immunological binding properties of the parent toward its identified target antigens, including the ability to bind to a unique anti-idiotypic antibody, AB1-2, whose epitopes consists of both the heavy and light chains of the parent antibody. The disclosure of that application also provides for single chain variable antibody fragments ("scFv"), $V_H$, $V_L$ and complementarity determining regions that selectively bind to oxidized phospholipids. The scFvs of the disclosure are soluble and can be readily synthesized. The disclosure of U.S. Pat. Publ. No. 20150376268A1 is incorporated herein by reference for all purposes.

In the studies presented herein, neutralization of OxPL by the in vivo endogenous expression of the EO6 antibody (using the EO6-scFv transgenic mouse) greatly inhibited atherosclerosis formation caused by TLR2 agonism. In particular, injections of the TLR2 agonist PAM3CSK4 into cholesterol-fed Ldlr$^{-/-}$ mice lead to dramatic enhancement of atherosclerosis. A similar set of injections into the EO6-scFv transgenic mice (on Ldlr$^{-/-}$ background) resulted in a significant inhibition of lesion formation.

In other studies presented herein, neutralization of OxPL can protect against a mouse model of Kawasaki Disease. Administration of the pathogen *Lactobaccilus casei* has been shown to cause Kawasaki-like disease in mice, with resultant enhanced atherosclerosis, coronary artery arteritis and abdominal aneurysms. This is TLR2 dependent, as administering *L. Casei* to TLR2 deficient mice had no disease-causing effect. Importantly, IL-1 has been shown to be involved, and as noted, OxPL are also a potent inducer of IL-1 release. Injection of *L. Casei* into the EO6 transgenic mice (in the Ldlr$^{-/-}$ background) under an identical protocol resulted in dramatic reductions not only in atherosclerosis, but of great relevance, in coronary arteritis as compared to injections into Ldlr$^{-/-}$ mice. The EO6 antibody does not directly bind *L. Casei* and therefore neutralizes the OxPL caused by the inflammatory effects associated with TLR2 mediated agonism. The development of coronary arteritis and subsequently coronary aneurysms has been a major and feared complication in children developing Kawasaki disease, and has been estimated to occur in up to 25% of children despite current therapy. Typically, Kawasaki disease is treated with intravenous immune globulin (IVIG) derived from pooled and purified human plasma, and aspirin (which is a generalized but non-specific anti-inflammatory therapy). Injections of high tittered humanized or human equivalent anti-OxPL antibody modified to enhance its biological effectiveness might then confer protection without any anticipated side effects, as such anti-OxPL antibodies are present in human B cell repertoire.

The experimental data thus demonstrates that atherosclerosis and inflammatory arteritis caused by TLR2 mediated agonism in vivo in mice can be prevented by neutralization of OxPL. TLR2 agonism has been implicated in numerous bacterial diseases of course, but also in a variety of so-called autoimmune mediated diseases such as lupus, rheumatoid arthritis, and others. The data demonstrates that neutralization of OxPL by the use of antibodies targeting the PC of OxPL can ameliorate or prevent many diseases that are accentuated or are influenced by activation of TLR2 mediated signaling pathways.

The disclosure provides use of antibodies, antibody fragments and humanized antibodies that bind to OxPL and which in some instances have the same or similar binding specificity as the EO6 antibody. Antibody fragments may be generated by traditional means, such as enzymatic digestion, or by recombinant techniques. In certain circumstances there are advantages of using antibody fragments, rather than whole antibodies. The smaller size of the fragments allows for rapid clearance, and may lead to improved access to tissue. In an acute setting, the half-life of antibody fragments is not critical. For a review of certain antibody fragments, see Hudson et al. (2003) Nat. Med. 9:129-134.

The disclosure, although providing specific antibody sequences and antibody sequence fragments having biological activity, further disclose that these sequences can be used to generate improved variants. Accordingly, in some instances an antibody or antibody fragment may have a percent identity to the sequences of the disclosure.

In some embodiments, amino acid sequence modification(s) of the antibodies described herein are contemplated. For example, it may be desirable to improve the binding affinity and/or other biological properties of the antibody. Amino acid sequence variants of the antibody may be prepared by introducing appropriate changes into the nucleotide sequence encoding the antibody, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired characteristics. The amino acid alterations may be introduced in the subject antibody amino acid sequence at the time that sequence is made.

The disclosure provides an antibody or antibody fragment capable of binding to OxPL or phosphorylcholine and/or a phosphorylcholine conjugate, wherein the antibody or antibody fragment comprises a variable heavy chain ($V_H$) domain and/or a variable light chain ($V_L$) domain, and wherein (a) the $V_H$ domain comprises an amino acid sequence that includes one, two or three complementarity determining regions (CDRs) selected from the group consisting of:

SEQ ID NO:6 and sequence that are at least 95%, 96%, 97%, 98%, 99% or 99.9% identical to SEQ ID NO:6;

SEQ ID NO:7 and sequence that are at least 95%, 96%, 97%, 98%, 99% or 99.9% identical to SEQ ID NO:7; and SEQ ID NO:8 and sequence that are at least 95%, 96%, 97%, 98%, 99% or 99.9% identical to SEQ ID NO:8;

(b) the $V_L$ domain comprises an amino acid sequence that includes one, two or three complementarity determining regions (CDRs) selected from the group consisting of:

SEQ ID NO:9 or 12 and sequence that are at least 95%, 96%, 97%, 98%, 99% or 99.9% identical to SEQ ID NO:9 or 12;

SEQ ID NO:10 and sequence that are at least 95%, 96%, 97%, 98%, 99% or 99.9% identical to SEQ ID NO:10; and SEQ ID NO:11 and sequence that are at least 95%, 96%, 97%, 98%, 99% or 99.9% identical to SEQ ID NO:11.

In one embodiment, the antibody or antibody fragment comprises a $V_H$ domain that comprises an amino acid sequence that includes CDRs comprising SEQ ID NO:6, 7 and 8, and/or the $V_L$ domain comprises an amino acid sequence that includes CDRs comprising SEQ ID NO:9, 10 and 11, or SEQ ID NO:10, 11 and 12.

In one embodiment, the disclosure provides an antibody or an scFv selected from the group consisting of: (a) an antibody or scFv with heavy and light chain domains comprising the complementarity determining regions of SEQ ID NO:6, 7, 8, 9, 10 and 11; and (b) an antibody or scFv with heavy and light chain domains comprising the complementarity determining regions of SEQ ID NO:6, 7, 8, 10, 11 and 12. In one embodiment either of (a) or (b) are linked to an Fc region.

In one embodiment, the disclosure provides an antibody comprising a light-chain variable region as set forth in SEQ ID NO:2 from amino acid 1 to about 146. In another embodiment, the disclosure provides an antibody with a humanized light chain variable region comprising the sequence of SEQ ID NO:4 from amino acid 1 to about 135. In another embodiment, the disclosure provides an antibody that comprises a heavy chain variable region comprising a sequence of SEQ ID NO:2 from about 162 to about 269. In another embodiment, the disclosure provides an antibody that comprises a humanized heavy chain variable region comprising a sequence of SEQ ID NO:4 from about 152 to about 258.

In another embodiment, the disclosure provides a chimeric antibody comprising, for example, a murine VH and/or VL and a human Fc region. For example, SEQ ID NO:14 provides the sequence of a chimeric antibody of the disclosure. In SEQ ID NO:14 amino acids 1-33 comprise and Ig kappa chain leader sequence for antibody secretion; amino acid 34-146 comprise an EO6 light-chain variable region; amino acids 147-161 provide a flexible linker sequence; amino acids 162-284 provide an EO6 heavy-chain variable region with a triple mutation of P201A, S224A and A225D relative to the wild-type urine EO6 antibody; amino acids 285-517 comprise an Fc region, in SEQ ID NO:14 the Fc region is a human IgG1-Fc with a modification of C290S and H294Y to increase ADCC activity. SEQ ID NO:14 also provide a further linker and His tag sequence, which one of skill in the art are optional (e.g., SEQ ID NO:14 from amino acid 518 to 528). The disclosure also contemplates and provides a coding sequence for SEQ ID NO:14 comprising SEQ ID NO:13. One of skill in the art can readily identify the nucleic acid sequence corresponding to the various domains identified above. The disclosure also includes a chimeric antibody sequence that is at least 90%, 95%, 96%, 97%, 98%, 99% or 99.9% identical to SEQ ID NO:14 from amino acid 1 to 284 linked to an Fc region from an different immunoglobulin (e.g., IgA, IgD, IgE, IgG, and IgM, or any of the subclasses (isotypes), e.g., $IgG_1$, $IgG_2$, $IgG_3$, $IgG_4$, $IgA_1$, and $IgA_2$).

In one embodiment, the disclosure provides an scFv comprising a linker between the light change variable region and the heavy-chain variable region. The linker can be any number of commonly used peptide linkers. In one embodiment, the linker comprises a repeating unit of GGGS (SEQ ID NO:5). The repeat of GGGS (SEQ ID NO:5) may be 2, 3, 4 or more times.

In another embodiment, the disclosure comprises a scFv comprising a light chain variable region of SEQ ID NO:2 from amino acid 1 to 146 linked by a peptide linker to a heavy chain variable region of SEQ ID NO:2 from amino acid 162 to about 269. In a specific embodiment, the scFv comprises a sequence of SEQ ID NO:2 form amino acid 1 to 269. In another embodiment, the disclosure provides for an scFv which has a polypeptide sequence of SEQ ID NO:2 from amino acid 1 to about 269 or 1 to about 303. In a further embodiment, the disclosure provides for an scFv that has a polypeptide sequence that has at least 75%, at least 80%, at least 85%, at least 90%, at least 95%, at least 98%, or at least 99% sequence identity to SEQ ID NO:2 from amino acid 1 to about 303 and which selectively binds to an oxidized phospholipid.

In yet further embodiments, fusion constructs comprising a first domain comprising SEQ ID NO:2 from amino acid 1 to about 269 or 1 to about 303 or a variant thereof is operably linked to a second domain comprising (i) a detectable label or (ii) a polypeptide of interest. One of skill in the art will recognize that such fusion constructs can be generated using chemical or molecular biology techniques that link a coding sequence comprising a sequence of SEQ ID NO:1 or variant thereof with a coding sequence of, for example, a polypeptide of interest. The coding sequences and domains may be separated by a linker or directly linked.

In yet another embodiment, the disclosure comprises a scFv comprising a light chain variable region of SEQ ID NO:4 from amino acid 1 to 135 linked by a peptide linker to a heavy chain variable region of SEQ ID NO:4 from amino acid 152 to about 258. In a specific embodiment, the scFv comprises a sequence of SEQ ID NO:4 form amino acid 1 to 258. In another embodiment, the disclosure provides for an scFv which has a polypeptide sequence of SEQ ID NO:4 from amino acid 1 to about 258 or 1 to about 263. In a further embodiment, the disclosure provides for an scFv that has a polypeptide sequence that has at least 75%, at least 80%, at least 85%, at least 90%, at least 95%, at least 98%, or at least 99% sequence identity to SEQ ID NO:4 from amino acid 1 to about 258 and which selectively binds to an oxidized phospholipid.

In yet further embodiments, fusion constructs comprising a first domain comprising SEQ ID NO:4 from amino acid 1 to about 258 or 1 to about 264 or a variant thereof is operably linked to a second domain comprising (i) a detectable label or (ii) a polypeptide of interest. One of skill in the art will recognize that such fusion constructs can be generated using chemical or molecular biology techniques that link a coding sequence comprising a sequence of SEQ ID NO:3 or variant thereof with a coding sequence of, for example, a polypeptide of interest. The coding sequences and domains may be separated by a linker or directly linked.

Nucleic acid molecules encoding the amino acid sequences of the antibodies, antibody fragments and variants of the antibody are prepared by a variety of methods known in the art. For preparing variants such methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

In a particular embodiment, the disclosure provides for a murine scFv which is encoded by a polynucleotide sequence of SEQ ID NO:1. In a further embodiment, the disclosure provides for a murine scFv which is encoded by a polynucleotide sequence that has at least 75%, at least 80%, at least 85%, at least 90%, at least 95%, at least 98%, or at least 99% sequence identity to SEQ ID NO:1 and which produces a polypeptide that selectively binds to oxidized phospholipids.

In another embodiment, the disclosure provides an scFv comprising a linker between the light change variable region and the heavy-chain variable region. The linker can be any number of commonly used peptide linkers. In one embodiment, the linker comprises a repeating unit of GGGS (SEQ ID NO:5). The repeat of GGGS (SEQ ID NO:5) may be 2, 3, 4 or more times.

The disclosure also encompasses humanized antibodies. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al. (1986) *Nature* 321:522-525; Riechmann et al. (1988) *Nature* 332:323-327; Verhoeyen et al. (1988) *Science* 239:1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies can be important to reduce antigenicity. According to the so-called "best-fit" method, the sequence of the variable domain of a rodent antibody is screened against the entire library of known human variable-domain sequences. The human sequence which is closest to that of the rodent is then accepted as the human framework for the humanized antibody. See, e.g., Sims et al. (1993) *J. Immunol.* 151:2296; Chothia et al. (1987) *J. Mol. Biol.* 196:901. Another method uses a particular framework derived from the consensus sequence of all human antibodies of a particular subgroup of light or heavy chains. The same framework may be used for several different humanized antibodies. See, e.g., Carter et al. (1992) *Proc. Natl. Acad. Sci. USA,* 89:4285; Presta et al. (1993) *J. Immunol.,* 151:2623.

It is further generally desirable that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

In a particular embodiment, the disclosure provides for a humanized scFv which is encoded by a polynucleotide sequence of SEQ ID NO:3. In a further embodiment, the disclosure provides for a humanized scFv which is encoded by a polynucleotide sequence that has at least 75%, at least 80%, at least 85%, at least 90%, at least 95%, at least 98%, or at least 99% sequence identity to SEQ ID NO:3 and which produces a polypeptide that selectively binds to oxidized phospholipids.

The disclosure further provides for a scFv disclosed herein that further comprises a fragment crystallizable region ("Fc") of an antibody. In a particular embodiment, the Fc region is from a human or humanized antibody. The Fc region is the tail region of an antibody that interacts with cell surface receptors called Fc receptors and some proteins of the complement system. This property allows antibodies to activate the immune system. In IgG, IgA and IgD antibody isotypes, the Fc region is composed of two identical protein fragments, derived from the second and third constant domains of the antibody's two heavy chains; IgM and IgE Fc regions contain three heavy chain constant domains (CH domains 2-4) in each polypeptide chain. The Fc regions of IgGs bear a highly conserved N-glycosylation site. Glycosylation of the Fc fragment is essential for Fc receptor-mediated activity. The N-glycans attached to this site are predominantly core-fucosylated diantennary structures of the complex type. In addition, small amounts of these N-glycans also bear bisecting GlcNAc and α-2,6 linked sialic acid residues. The other part of an antibody, called the Fab region, contains variable sections that define the specific target that the antibody can bind. The scFv of the disclosure are comprised of elements from the Fab region. By contrast, the Fc region of all antibodies in a class are the same for each species; they are constant rather than variable. The Fc region is, therefore, sometimes termed the "fragment constant region". Accordingly, the polynucleotide and polypeptide sequences which encode the Fc regions for countless species have already been determined and would be known by one of skill in the art. In a particular, embodiment, the disclosure provides for an scFv polynucleotide sequence disclosed herein that further comprises a polynucleotide sequence which encodes an Fc region from IgG antibody (e.g., from a human IgG antibody). In a further embodiment, the disclosure provides for an scFv polypeptide sequence disclosed herein that further comprises a polypeptide sequence of an Fc region from an IgG antibody.

In a particular, embodiment, the disclosure provides for a scFv polynucleotide sequence disclosed herein that further comprises a polynucleotide sequence which encodes an Fc region from IgG antibody (e.g., from a human IgG antibody). In a further embodiment, the disclosure provides for an scFv polypeptide sequence disclosed herein that further comprises a polypeptide sequence of an Fc region from an IgG antibody. In one embodiment the coding sequence for the Fc region comprises a sequence as set forth in SEQ ID NO:3 from about nucleotide 790 to about nucleotide 1518.

In a further embodiment, the disclosure provides for a vector which comprises a polynucleotide sequence encoding a scFv as set forth above with reference to SEQ ID NO:1 and 3, or sequences having sequence identity of at least 99%, at least 95%, at least 90%, at least 85%, at least 80%, at least 75% or at least 70% identity to SEQ ID NO:1 or SEQ ID NO:3.

The disclosure also provides a humanized antibody that has the binding specificity of an EO6 antibody. The humanized antibody comprises (i) a sequence as set forth in SEQ ID NO:4 from amino acid 1 to about amino acid 506 or (ii) a sequence that is at least 90%, 91%, 92%, 93%, 94%, 95%, 96%, 97%, 98%, 99%, 99.5% or 99.8% identical to SEQ ID NO:4 from amino acid 1 to about 506.

The disclosure also provides a polynucleotide that encodes a humanized antibody of the disclosure. The polynucleotide comprises a sequence selected from the group consisting of (i) a polynucleotide that encodes SEQ ID NO:4, (ii) a polynucleotide that hybridizes under stringent conditions to a polynucleotide consisting of SEQ ID NO:3 and encodes a humanized antibody that binds to OxPL with a specificity substantially similar to the EO6 antibody, (iii) a polynucleotide that is at least 90%, 91%, 92%, 93%, 94%, 95%, 96%, 97%, 98%, 99%, 99.5% or 99.8% identical to SEQ ID NO:3 and which encodes an antibody that binds to OxPL with a specificity substantially similar to the EO6 antibody; (iv) a polynucleotide as set forth in SEQ ID NO:3; (v) a polynucleotide of any of (i) to (iv) wherein the polynucleotide comprises RNA.

Polynucleotide sequences encoding polypeptide components of the antibody or antibody fragments of the disclosure can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. Coli* is typically transformed using pBR322, a plasmid derived from an *E. Coli* species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage vectors may be utilized in making a recombinant vector which can be used to transform susceptible host cells such as *E. Coli* LE392.

The expression vector of the disclosure may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the (3-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al., (1980) *Cell* 20: 269) using linkers or adaptors to supply any required restriction sites.

In another embodiment, the production of the immunoglobulins according to the disclosure can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the *E. Coli* trxB-strains) provide cytoplasm conditions that are favorable for disulfide bond formation, thereby permitting proper folding and assembly of expressed protein subunits. Proba and Pluckthun *Gene,* 159:203 (1995).

Prokaryotic host cells suitable for expressing antibodies of the invention include Archaebacteria and Eubacteria, such as Gram-negative or Gram-positive organisms. Examples of useful bacteria include *Escherichia* (e.g., *E. Coli*), *Bacilli* (e.g., *B. subtilis*), *Enterobacteria, Pseudomonas* species (e.g., *P. aeruginosa*), *Salmonella typhimurium, Serratia marcescans, Klebsiella, Proteus, Shigella, Rhizobia, Vitreoscilla,* or *Paracoccus*. In one embodiment, gram-negative cells are used. In one embodiment, *E. Coli* cells are used as hosts for the disclosure. Examples of *E. Coli* strains include strain W3110 (Bachmann, Cellular and Molecular Biology, vol. 2 (Washington, D.C.: American Society for Microbiology, 1987), pp. 1190-1219; ATCC Deposit No. 27,325) and derivatives thereof, including strain 33D3 (U.S. Pat. No. 5,639,635). Other strains and derivatives thereof, such as *E. Coli* 294 (ATCC 31,446), *E. Coli* B, *E. ColiX* 1776 (ATCC 31,537) and *E. Coli* RV308 are also suitable. These examples are illustrative rather than limiting. Methods for constructing derivatives of any of the above-mentioned bacteria having defined genotypes are known in the art and described in, for example, Bass et al., *Proteins,* 8:309-314 (1990). It is generally necessary to select the appropriate bacteria taking into consideration replicability of the replicon in the cells of a bacterium. For example, *E. Coli, Serratia,* or *Salmonella* species can be suitably used as the host when well-known plasmids such as pBR322, pBR325, pACYC177, or pKN410 are used to supply the replicon. Typically, the host cell should secrete minimal amounts of proteolytic enzymes, and additional protease inhibitors may desirably be incorporated in the cell culture.

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extra-chromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the disclosure are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol. The prokaryotic host cells are cultured at suitable temperatures.

In one embodiment, the expressed polypeptides are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay. Large scale or small-scale fermentation can be used and can be optimized using skills well known in the art.

Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration.

The disclosure further provides for an expression vector which encodes an antibody, antibody fragment or polypeptide disclosed herein that is transferred into a suitable host organism. The suitable host organism is a microorganism, yeast or a mammalian cell system. Typically, the mammalian cell system is monocyte-derived (e.g., macrophages, monocytes, and neutrophils), lymphocyte-derived (e.g., myeloma, hybridoma, and a normal immortalized B cell), parenchymal (e.g., hepatocytes) and non-parenchymal cells (e.g., stellate cells).

The disclosure also provides for pharmaceutical compositions or formulations which comprise a therapeutically effective amount of an antibody, antibody fragment or polypeptide of the disclosure. The pharmaceutical compositions or formulations may further comprise carriers, excipients, diluents, solubilizers, stabilizers, buffers, tonicity modifiers, bulking agents, viscosity enhancers/reducers, surfactants, chelating agents, and adjuvants.

A "therapeutically effective amount" of a substance/molecule of the disclosure, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects.

A "prophylactically effective amount" refers to an amount effective, at dosages and for periods of time necessary, to achieve the desired prophylactic result. Typically, but not necessarily, since a prophylactic dose is used in subjects prior to or at an earlier stage of disease, the prophylactically effective amount will be less than the therapeutically effective amount.

Therapeutic formulations comprising an antibody or fragment thereof of the disclosure are prepared for storage by mixing the antibody or fragment having the desired degree of purity with optional physiologically acceptable carriers, excipients or stabilizers (Remington: The Science and Practice of Pharmacy 20th edition (2000)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants or polyethylene glycol (PEG).

The pharmaceutical compositions disclosed herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

The pharmaceutical compositions disclosed herein may be formulated in any dosage forms that are suitable for parenteral administration, including solutions, suspensions, emulsions, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, dimethylacetamide, and dimethylsulfoxide.

In one embodiment, the pharmaceutical compositions disclosed herein are formulated as ready-to-use sterile solutions. In another embodiment, the pharmaceutical compositions are disclosed herein are formulated as sterile dry soluble products, including powders and hypodermic tablets, which, if so necessary, may be reconstituted with a vehicle prior to use. In yet another embodiment, the pharmaceutical compositions are disclosed as ready-to-use sterile suspensions. In yet another embodiment, the pharmaceutical compositions are disclosed as sterile dry insoluble products to be reconstituted with a vehicle prior to use. In still another embodiment, the pharmaceutical compositions are disclosed as ready-to-use sterile emulsions.

The pharmaceutical compositions may be formulated as a suspension, solid, semi-solid, or thixotropic liquid, for administration as an implanted depot. In one embodiment, the pharmaceutical compositions disclosed herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers, such as hydrogels of esters of acrylic and methacrylic acid, collagen, cross-linked polyvinylalcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy 20th edition (2000).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the immunoglobulin of the invention, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and yethyl-L-glutamate, non-degradable ethylene-vinyl acetate, degradable lactic acid-glycolic acid copolymers such as the LUPRON DEPOT (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated immunoglobulins remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The antibodies, antibody fragments and polypeptides disclosed herein bind to OxPLs and block their pro-inflammatory effects. It is anticipated that the in vivo use of an antibody, antibody fragment or polypeptide of the disclsoure to blockade OxPL biological effects in many different situations. For example, it has been shown that OxPLs are generated by macrophages and other cells via a TLR2-mediated mechanism. These released OxPLs could bring about adverse vasoactive effects throughout the patient's body. Acute and/or chronic injection/infusion of an antibody, antibody fragment or polypeptide of the disclosure therefore could block these adverse effects and/or alternatively block or attenuate similar inflammatory events, resulting from TLR2 activation. Similarly, an antibody, antibody fragment, or polypeptide of the disclosure could also be infused to a subject so as to block proinflammatory effects mediated by OxPLs generated from a variety of pathological conditions, such as viral or bacterial infections, or autoimmune disorders. Accordingly, an antibody, antibody fragment of polypeptide of the disclosure would be effective as anti-inflammatory agents in other systemic inflammatory settings mediated by TLR2 activation, such as in rheumatoid arthritis. Accordingly, an antibody, antibody fragment of polypeptide of the disclosure can be used in many clinical applications or settings where anti-inflammatories and/or anti-atherosclerotic agents need to be administered temporally and/or chronically.

The disclosure provides methods of treatment using an antibody, antibody fragment, and polypeptides of the disclosure to treat a subject with a TLR2-mediated disease or disorder. In a particular embodiment, the disclosure provides for treating a TLR2-mediated disease or disorder with a therapeutically effective amount of an antibody, antibody fragment, or polypeptide of the disclosure. Examples of TLR2-mediated diseases or disorders include, but are not limited to, Kawasaki disease (Kang et al., *Korean J Pediatr* 60(7):208-215 (2017)), type 2 diabetes (Sepehri et al., *Cell Mol Biol Lett* 21:2 (2016)), rheumatoid arthritis (McGarry et al., *Arthritis Res Ther* 17:153 (2015)), dermatologic disease (Kang et al., *Journal of American Academy of Dermatology*, 54(6):951-983 (2006)), multiple sclerosis (Hossain et al., *Oncotarget* 6(34):35131-35132 (2015)), systemic lupus erythematosus (Liu et al., *European Journal of Immunology*, 45(9):2683-2693 (2015)), ulcerative colitis (Folova et al., *Journal of Histochemistry & Cytochemistry* 56(3):267-274 (2008), Graves Disease (Peng et al., *Front Immunol,* 7:578 (2016)), Sjögren's syndrome (Sisto et al., Clin Exp Med 17(3):341-350 (2017), autoimmune thyroid diseases (Peng et al., *Front Immunol* 7:547 (2016), and vasculitis (Summers et al., *Arthritis Rheum* 63(4):1124-35 (2011)). In a particular embodiment, the disclosure provides for treating a subject with Kawasaki disease with a therapeutically effective amount of an antibody, antibody fragment, or a polypeptide of the disclosure For use in the therapeutic applications described herein, kits and articles of manufacture are also described herein. Such kits can comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers can be formed from a variety of materials such as glass or plastic.

For example, the container(s) can comprise one or more antibodies, antibody fragments, or polypeptides described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprise an identifying description or label or instructions relating to its use in the methods described herein.

A kit will typically comprise one or more additional containers, each with one or more of various materials (such as reagents, optionally in concentrated form, and/or devices) desirable from a commercial and user standpoint for use of a compound described herein. Non-limiting examples of such materials include, but are not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself, a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein. These other therapeutic agents may be used, for example, in the amounts indicated in the Physicians' Desk Reference (PDR) or as otherwise determined by one of ordinary skill in the art.

The following examples are intended to illustrate but not limit the disclosure. While they are typical of those that might be used, other procedures known to those skilled in the art may alternatively be used.

EXAMPLES

Materials. Synthetic standards 1,2-dinonanoyl-sn-glycero-3-phosphocholine (DNPC), 1-palmitoyl- 2-(5-oxovaleroyl)-sn-glycero-3-phosphocholine (POVPC), 1-palmitoyl-2-glutaroyl-sn-glycero-3- phosphocholine (PGPC), 1-Palmitoyl-2-azelaoyl-sn-glycero-3-phosphocholine (PAzPC), 1- palmitoyl-2-(9-oxo)nonanoyl-sn-glycero-3-phosphocholine (PONPC), and the IgM murine natural antibody EO6, which is LPS free, were obtained from Avanti Polar Lipids (Alabaster, Ala.). 1-(palmitoyl)-2-(5-keto-6-octene-dioyl)-3-phosphocholine (KOdiAPC) and, 1-palmitoyl-2- (4-keto-dodec-3-ene-dioyl)-sn-glycero-3-phosphocholine (KDdiAPC) were purchased from Cayman Chemicals (Ann Arbor, Mich.). All solvents were HPLC grade.

Generation and characterization of EO6-scFv transgenic mice. The generation of transgenic C57BL/6 mice expressing the T15/EO6 idiotype as a single chain variable antibody fragment-termed EO6-scFv-Tg. In brief, the cDNAs encoding EO6 variable regions of the heavy and light chains were linked with a 15-amino acid peptide by overlapping PCR, and cloned into an expression vector pSecTag2A (Invitrogen) containing a murine Ig kappa-chain leader sequence for secretion and c-myc and polyHis as epitope tags. HEK293 cells were transfected and the binding properties of EO6-scFv secreted into culture supernatant were shown to mimic those of the intact EO6. The same construct was then cloned into the liver-specific expression vector pLiv7 and used to generate transgenic (Tg) mice in the C57BL/6 background expressing the EO6-scFv transgene driven by the apoE promoter. Offspring were screened both for plasma EO6-scFv titer and integration of the transgene by PCR amplification of the tail DNA. The transgenic EO6-scFv founder lines were bred with each other to generate "homozygous" transgenic mice, and in turn, these were crossed into $Ldlr^{-/-}$ mice on the C57BL/6 background. All animals were genotyped for EO6-scFv and $Ldlr^{-/-}$, respectively and plasma assayed to confirm expression of the EO6-scFv by immunoassay. The EO6-scFv mRNA was strongly expressed in liver, peritoneal macrophages and spleen, and to a lesser extent in heart. Plasma levels of the EO6-scFv averaged 20-30 µg/ml in these studies.

OxPL mass spectrometry. PC-containing phospholipids were extracted from NNCM. Cell media was removed, and cells were washed with PBS. Each well was scraped into 1 mL of methanol/acetic acid (3% v/v) solution containing 0.01% BHT and transferred to a 10 mL glass conical tube and capped under $N_2$ (g). Ten nanograms of DNPC was added as internal standard into each sample for quantitation purposes. Two milliliters of hexane containing BHT was added to the tube, capped under $N_2$ (g), vortexed for five seconds, and then centrifuged for 5 min at 3500 rpm at 4° C. The upper hexane layer was then siphoned off using a glass Pasteur pipette and discarded.

The hexane/BHT wash was repeated three times, capping under $N_2$ (g), vortexing for five seconds, and centrifuging after each wash. After the final hexane/BHT wash, 2 mL of chloroform containing BHT and 750 µL of PBS were added to the tube then vortexed and centrifuged as described above. The lower organic layer was removed using a glass Pasteur pipette and transferred to a clean 15 mL glass conical tube where the solution was aspirated off using a nitrogen evaporator, and then reconstituted into 300 µL of chloroform/methanol (2:1 v/v) for storage at −80° C.

The separation of OxPLs was carried out using reverse-phase (RP) chromatography. Extracted hearts were reconstituted in RP eluent consisting of 60:40 acetonitrile:water, 10 mM ammonium formate and 0.1% formic acid immediately prior to injection. Thirty microliters of the sample were injected onto an Ascentis Express C18 HPLC column (15 cm×2.1 mm, 2.7 µm; Supelco Analytical, Bellefonte, Pa., USA) with separation by a Prominence UFLC system from Shimadzu Corporation (Canby, Oreg., USA). Elution was performed using a linear gradient of solvent A (acetonitrile/water, 60:40 v/v) and solvent B (isopropanol/acetonitrile, 90:10, v/v) with both solvents containing 10 mM ammonium formate and 0.1% formic acid. The mobile phase composition that was used is as follows: initial solvent B at 32% until 4.00 min; switched to 45% B; 5.00 min 52% B; 8.00 min 58% B; 11.00 min 66% B; 14.00 min 70% B; 18.00 min 75% B; 21.00 min 97% B; 25.00 min 97% B; 25.10 min 32% B. A flow rate of 260 µl/min was used for analysis, and the sample tray and column oven were held at 4 and 45° C., respectively.

Detection of OxPL was carried out by mass spectrometry in positive polarity mode. MRM scans were performed on 6 transitions using a product ion of 184.3 m/z, corresponding to the cleaved phosphocholine moiety. Six commercially available standards of PONPC, POVPC, PGPC, PAzPC, KOdiAPC, and KDdiAPC were injected and accurate peak assignments were based upon retention times and mass transitions. The mass spectrometry settings were as follows: curtain gas, 26 psi; collision gas, medium; ion spray voltage, 5500 V; temperature, 500.0° C.; ion source gas 1, 40.0 psi; ion source gas 2, 30.0 psi; declustering potential, 125 V, entrance potential, 10 V; collision energy, 53 V; collision cell exit potential, 9 V; and dwell time, 50 msec. External mass calibration was performed at regular intervals. For quantitation, multiple reaction monitoring (MRM) calibration curves were made for each of the 6 commercially available OxPL standards and peaks were normalized based on their relative responses. Ten nanograms of internal standard was added to all samples during extraction. A 4000 QTRAP® triple quadrupole mass spectrometer system with a Turbo V electrospray ion source from AB Sciex (Framingham, Mass., USA) was coupled to the liquid chromatography system.

Development of Abdominal Aorta Aneurysms and Dilatation in LCWE Induced KD Vasculitis Mouse Model. Kawasaki disease causes persistent coronary arteritis (CA) in young children and is recognized as the leading cause of acquired heart disease in children in the developed world today. In the animal model, *Lactobacillus casei* cell wall extract (LCWE) induced CA in mice accurately mimics the pathogenesis of KD in humans. Group B *L. casei* (ATCC 11578) were grown in *Lactobacillus* MRS broth, harvested by centrifugation during the exponential growth phase, and washed with PBS at pH 7.40. After harvested, the cells were treated overnight with 4% SDS, and then sequentially incubated with 250 ug/ml RNase, DNaseI, and trypsin. The final pellet was then sonicated (5 g packed wet weight in 15 ml PBS) for 2 h at a pulse setting of 9 s pulse/5 s pause at 20 kHz frequency (Vibra Cell, Sonics & Materials Inc., Newtown, Conn.). Following 1 h centrifugation at 20,000 xg, the supernatant concentration was determined on the basis of its rhamnose content by using a phenol-sulfuric acid colorimetric assay (Dubois et al. 1956). The endotoxin concentration of this preparation was <1.5 µg/µg, as determined by the Limulus amoebocyte lysate assay (Associates of Cape Cod Inc., East Falmouth, Mass.).

Four-week old C57/BL6 mice were injected with 250 ug of LCWE in PBS or with saline alone. Mice were sacrificed at 4-time points of 7, 14, 21 and 28 day. The abdomiminal and coronary arteries were identified in serial sections (7 µm), fixed with formalin, and stained with hematoxylin and eosin. For the immunohistochemical analysis, sections were pre-treated with 0.3% hydrogen peroxide in PBS for 30 min. Inflammatory marker antibodies or isotype control antibodies were applied in 0.5% bovine serum albumin in PBS at 1:100 for 1 hr. Slides were then washed and biotinylated horseradish peroxidase conjugated secondary antibody (Vector Lab, Burlingame, Calif.) was applied at 1:500 for 30 min, washed and stained with streptavidin conjugated horseradish peroxidase at 1:1,000 for 30 min. Immunohistochemical staining was detected using the SK-4100 DAB kit, as per manufacturer's instructions (Vector Lab). The data showed that LCWE-induced AAA formation and intense inflammatory histology in EO6-Tg mice were significantly reduced compared to the control mice (FIG. 17-FIG. 21).

Serum inflammatory cytokine assays. The Bio-Plex Pro Mouse Cytokine 23-Plex Immunoassay kit (Bio-Rad Laboratories, Inc.) was used to detect different cytokines simultaneously in the plasma of Ldlr$^{-/-}$ or Ldlr$^{-/-}$/EO6 scFv-Tg mice treated with LCWE and placed on HFC diet for 12 weeks. Measurements and data analysis of all assays were performed based on the protocol of Bio-Plex system in combination with the Bio-Plex Manager software. Results are shown in FIG. 10. Compared to Ldlr$^{-/-}$ mice (n=7-10), Ldlr$^{-/-}$ EO6-scFv-Tg mice (n=7-10) showed that the plasma levels of certain pro-inflammatory cytokines/chemokines (TNF-alpha, CCL2, CCL5, CXCL1, IL6 and IL12) were significantly decreased by multiplex Bio-Plex (Bio-Rad) assays, indicating a generalized decrease in systemic inflammation in EO6scFv-TG Ldlr$^{-/-}$ mice.

A number of embodiments have been described herein. Nevertheless, it will be understood that various modifications may be made without departing from the spirit and scope of this disclosure. Accordingly, other embodiments are within the scope of the following claims.

---

What is claimed is:

1. A method of treating a subject with Kawasaki disease, comprising administering to the subject a therapeutically effective amount of an antibody, antibody fragment, or polypeptide that binds specifically to an oxidative phospholipid (OxPL), wherein the antibody, antibody fragment or polypeptide inhibits a biological activity of the OxPL; and wherein the antibody, antibody fragment or polypeptide comprises: a variable heavy chain domain (VH) comprising the complementarity determining regions (CDRs) of the VH amino acid sequence set forth in SEQ ID NO:2; and a variable light chain domain (VL) comprising the CDRs of the VL amino acid sequence set forth in SEQ ID NO:2 or 4.

2. The method of claim 1, wherein the method further comprises administering to the subject an additional therapeutic agent.

3. The method of claim 1, wherein the method further comprises administering to the subject Intravenous immunoglobulin (IVIG) and/or salicylates.

4. The method of claim 1, wherein the subject is a human subject that is less than five years old.

5. The method of claim 1, wherein the biological activity of the OxPL comprises activation of CD36-TLR2 apoptosis pathway.

6. The method of claim 1, wherein the antibody, antibody fragment, or polypeptide is a single-chain variable fragment (ScFv).

7. The method of claim 1, wherein the antibody, antibody fragment or polypeptide is administered intravascularly.

8. The method of claim 1, wherein the VH and/or VL are linked to an Fc or FC2 region.

9. The method of claim 1, wherein: the VH comprises the CDR amino acid sequences set forth in SEQ ID NO:6, 7 and 8; and the VL comprises the CDR amino acid sequences set forth in SEQ ID NO:9, 10 and 11.

10. The method of claim 9, wherein: the VH comprises an amino acid sequence that is at least 95% identical to the VH amino acid sequence set forth in SEQ ID NO:2; and the VL comprises an amino acid sequence that is at least 95% identical to the VL amino acid sequence set forth in SEQ ID NO:2.

11. The method of claim 9, wherein: the VH comprises the VH amino acid set forth in SEQ ID NO:2; and the VL comprises the VL amino acid sequence set forth in SEQ ID NO:2.

12. The method of claim 1, wherein: the VH comprises the CDR amino acid sequences set forth in SEQ ID NO:6, 7 and 8; and the VL comprises the CDR amino acid sequences set forth in SEQ ID NO: 12, 10 and 11.

13. The method of claim 12, wherein: the VH comprises an amino acid sequence that is at least 95% identical to the VH amino acid sequence set forth in SEQ ID NO:4; and the VL comprises an amino acid sequence that is at least 95% identical to the VL amino acid sequence set forth in SEQ ID NO:4.

14. The method of claim 12, wherein: the VH comprises the VH amino acid set forth in SEQ ID NO:4; and the VL comprises the VL amino acid sequence set forth in SEQ ID NO:4.

* * * * *